United States Patent [19]
Shinohara et al.

[11] Patent Number: 5,735,798
[45] Date of Patent: Apr. 7, 1998

[54] TOILET-INSTALLED DIGITAL SPHYGMOMANOMETER WITH RETRACTABLE CUFF

[75] Inventors: Kuniaki Shinohara; Takanori Matsuno; Yoshiki Hiruta; Keisuke Kanzaki; Kentaro Todoroki, all of Kita-kyushu, Japan

[73] Assignee: Toto Ltd., Fukuoka, Japan

[21] Appl. No.: 557,007

[22] PCT Filed: Mar. 14, 1995

[86] PCT No.: PCT/JP95/00420

§ 371 Date: Feb. 20, 1996

§ 102(e) Date: Feb. 20, 1996

[87] PCT Pub. No.: WO95/26159

PCT Pub. Date: Oct. 5, 1995

[30] Foreign Application Priority Data

Mar. 25, 1994 [JP] Japan ................ 6-079800
Mar. 25, 1994 [JP] Japan ................ 6-079801

[51] Int. Cl.$^6$ ................................ A61B 5/00
[52] U.S. Cl. ............... 600/490; 600/494; 600/500; 4/314; 4/420; 4/661
[58] Field of Search ............... 4/314, 318, 443, 4/444, 420, 661; 128/766, 771, 686, 687, 681, 677, 672

[56] References Cited

U.S. PATENT DOCUMENTS

| | | | |
|---|---|---|---|
| 4,961,431 | 10/1990 | Ikenega et al. | 128/771 |
| 4,962,550 | 10/1990 | Ikenega et al. | 4/314 |
| 4,982,741 | 1/1991 | Saito et al. | 128/771 |
| 5,111,539 | 5/1992 | Hiruta et al. | |
| 5,119,829 | 6/1992 | Saito et al. | 128/771 |
| 5,184,359 | 2/1993 | Tsukamura et al. | 128/760 |
| 5,410,471 | 4/1995 | Alyfuku et al. | 128/708 |

FOREIGN PATENT DOCUMENTS

| | | | |
|---|---|---|---|
| 61-234841 | 10/1986 | Japan | 128/771 |
| 61-290935 | 12/1986 | Japan | 128/771 |
| 63-6291 | 2/1988 | Japan | |
| 64-6909 | 1/1989 | Japan | 128/771 |
| 2-123204 | 10/1990 | Japan | 128/771 |
| 3-39003 | 4/1991 | Japan | 128/771 |
| 4193157 | 7/1992 | Japan | 128/771 |

OTHER PUBLICATIONS

PCT/ISA/210, International Search Report, Japanese Patent Office, (Jun. 20, 1995).

Primary Examiner—Robert L. Nasser
Attorney, Agent, or Firm—Finnegan, Henderson, Farabow, Garrett & Dunner, L.L.P.

[57] ABSTRACT

A toilet-installed digital sphygmomanometer provided with retractable cuffs. A housing (36) is arranged laterally of a toilet seat and two occluding finger cuffs (62) different in size are mounted to associated respective sliders (70) in a manner movable relative to the housing (36). In use, one of the sliders is moved to permit a cuff (62), of a size suited to the size of the user's finger, to protrude out of the surface of the housing (36) for engagement by the finger. When not in use, all the cuffs are retracted within the housing so that the cuffs are kept clean. In another embodiment, a plurality of pivoting arms are hinged to the housing and the cuffs different in size are mounted, respectively, to the associated pivoting arms. In still another embodiment, a plurality of cuffs different in size are mounted to a revolving member journaled to the housing and a particular cuff is selected by rotating the revolving member.

18 Claims, 22 Drawing Sheets

TOILET-INSTALLED DIGITAL SPHYGMOMANOMETER WITH RETRACTABLE CUFF

TECHNICAL FIELD

The present invention relates to an improvement in a digital sphygmomanometer of the type installed in a toilet to perform the measurement of artery blood pressure and pulse rate at the toilet.

BACKGROUND ART

Inview of the trends for longevity of the individuals, the importance of health care and maintenance has been receiving increasing attention. In order to assist the individuals in rendering their health check at home, various health monitoring and measuring instruments for domestic use have been provided which includes a sphygmomanometer. As the artery blood pressure generally fluctuates from time to time during the day and also varies in accordance with the condition of the activity of the individuals, it is recommended that the artery pressure measurement be carried out and the results recorded each day at a given time and under the same physical condition. Accordingly, there has been proposed in the art a toilet-installed sphygmomanometer which is capable of performing the artery blood pressure measurement by making use of a toilet which is used every morning periodically.

As disclosed, for example, in U.S. Pat. No. 5,111,539 to Hiruta et al., the toilet-installed sphygmomanometer proposed in the art includes a housing in the form of an arm rest disposed laterally of a toilet seat, with an occluding finger cuff being arranged on the housing to permit the user to engage a finger therein to perform the measurement of the artery blood pressure and pulse rate.

In the conventional digital (i.e., finger type) sphygmomanometer of this type, the cuff is exposed upwardly of the upper surface of the housing to permit the user to insert the finger into the cuff while resting the palm upon the housing. As a result, when the digital sphygmomanometer is not in use, the cuff hinders routine use of the toilet as well as cleaning of the housing. Also, the cuff is susceptible to be fouled as it is exposed out of the housing. A compression bladder arranged inside of the cuff is difficult to clean if once fouled.

The primary object of the invention is to provide an improved toilet-installed digital sphygmomanometer which is convenient to use and wherein the cuff can be kept hygienically. Another object of the invention is to provide a toilet-installed digital sphygmomanometer which has a simple and neat appearance.

Another problem associated with the conventional toilet-installed sphygmomanometer is that it is equipped only with a single cuff of a given size. In this regard, it is desirable that the toilet-installed sphygmomanometer may be used in common throughout all the members of a family regardless of age or sex. However, the thickness (i.e., diameter) of a finger varies considerably from adults to children as well as from male to female. If a large-sized cuff suitable for use with a male's large finger had been prepared, it would be impossible to effectively occlude the artery of a slender finger such as the ones of a female. Accordingly, given a single cuff of a predetermined size, it has been difficult to carry out the artery blood pressure measurement with a high degree of accuracy.

Accordingly, another object of the invention is to provide a toilet-installed sphygmomanometer which is equipped with a plurality of cuffs of different size accommodating fingers of different diameter.

DISCLOSURE OF THE INVENTION

The feature of the present invention resides in the provision for a movable support member for supporting the cuff for movement between an operative position in which the cuff is emerged out of the housing and a rest position in which the cuff is retracted substantially within the housing. In use, the cuff is protruded out of the housing to enable the user to engage the finger therewith. When not in use, the cuff may be retracted within the housing for storage therein. Therefore, the cuff does not obstruct the routine use of the toilet so that the toilet equipped with the sphygmomanometer according to the invention is convenient to use. Furthermore, the cuff is free from fouling since it is retracted within the housing when not in use. When the cuff is not in use, the housing is neat in appearance and may be easily cleaned whenever desired.

In an embodiment of the invention, the movable support member includes a slider mounted slidably to the housing, with the cuff being in turn mounted to the slider.

Preferably, the housing is provided with two or more sliders to which two or more cuffs different in size are mounted respectively. With this arrangement, it is possible to selectively use a cuff having an optimal size suited to the diameter of the finger of a particular user so that the blood pressure measurement is performed with a high degree of accuracy while enjoying the benefit of the retractable cuffs.

Where a plurality of cuffs and associated sliders are used, it is preferable to connect respective cuffs to a single common air pump through associated respective shut-off valves which are opened and closed in response to the movement of the associated sliders. With this arrangement, air under pressure is applied to the compression bladder of a particular selected cuff only when the latter is brought into its operative position, thereby avoiding the risk of inadvertently inflating another bladder pertaining to the non-selected cuff. Accordingly, the service life of the bladders is prolonged.

Alternatively, where a single slider is used, a plurality of cuffs different in size may be detachably mounted to the housing and a cuff of a proper size selected by the user may be mounted to the slider.

In another embodiment of the invention, the movable support member includes a revolving member journaled for rotational movement to the housing. The revolving member has a generally triangular, generally quadrangular or other polygonal cross-section, with one or more cuffs being mounted, respectively, to the outer surfaces of the revolving member. Upon rotation of the revolving member at a predetermined angle, one of the cuffs is emerged out of the housing. By rotating the revolving member at another angle, that cuff is retracted within the housing and another cuff different in size is emerged. When not in use, the revolving member may be rotated until one of the outer surfaces which is not provided with the cuff is brought in flush with the outer surface of the housing.

In still another embodiment of the invention, the movable support member includes one or more pivoting arms, each having a frontal end pivoted to the housing and a rear end to which the associated cuff is mounted.

These features and advantages of the invention, as well as other features and advantages thereof, will become apparent from the following description made with reference to the preferred embodiments thereof.

BRIEF DESCRIPTION OF THE DRAWINGS

FIG. 24 is an enlarged perspective view, partly cut away, of the cuff shown in. FIG. 20;

Throughout different views, identical or similar parts and members are indicated by like reference numerals.

BEST MODE FOR CARRYING OUT THE INVENTION

Figure 1:
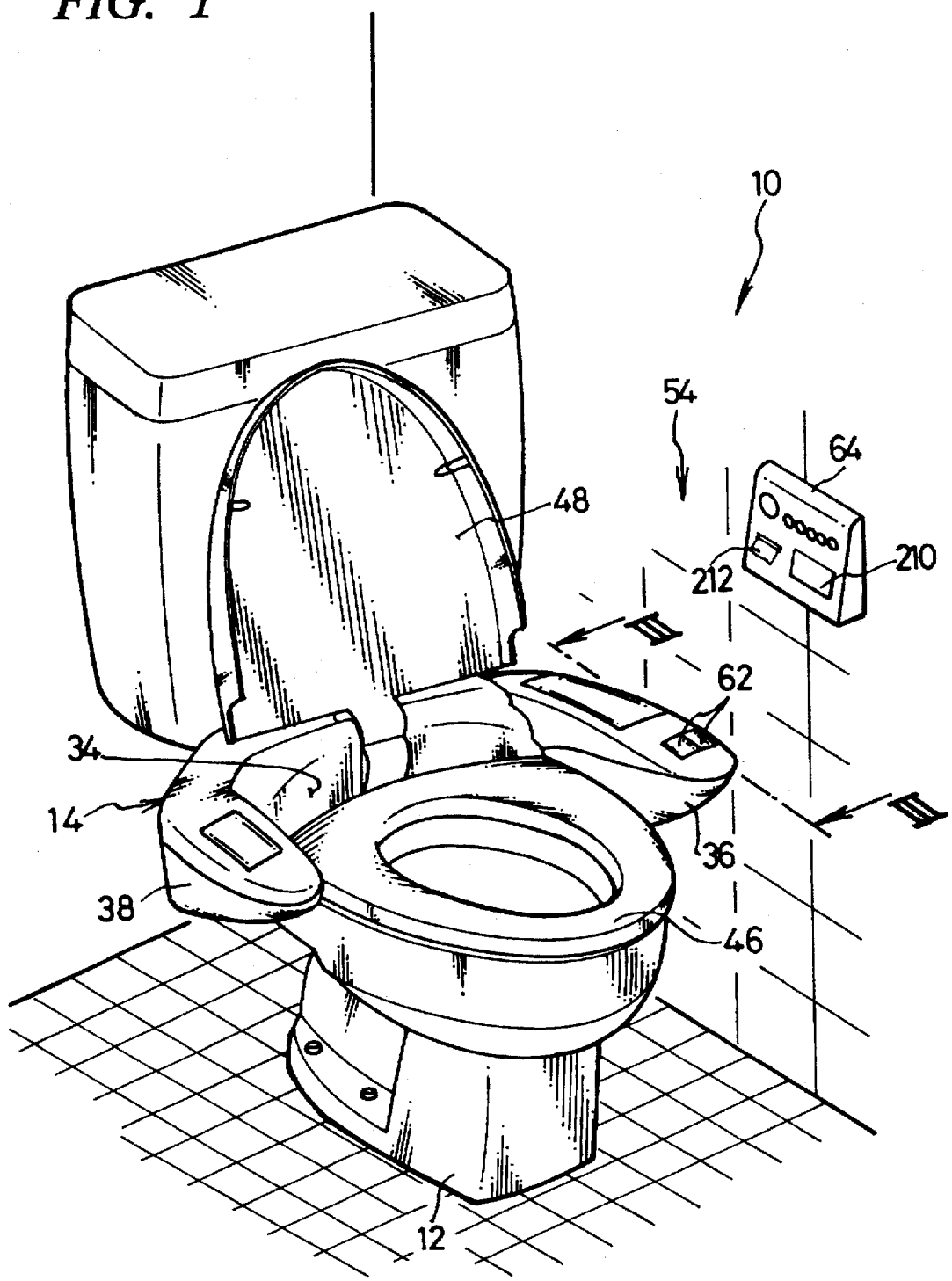
FIG. 1 is a perspective view showing the sphygmomanometer according to the first embodiment of the invention as installed in a toilet.
Figure 2:
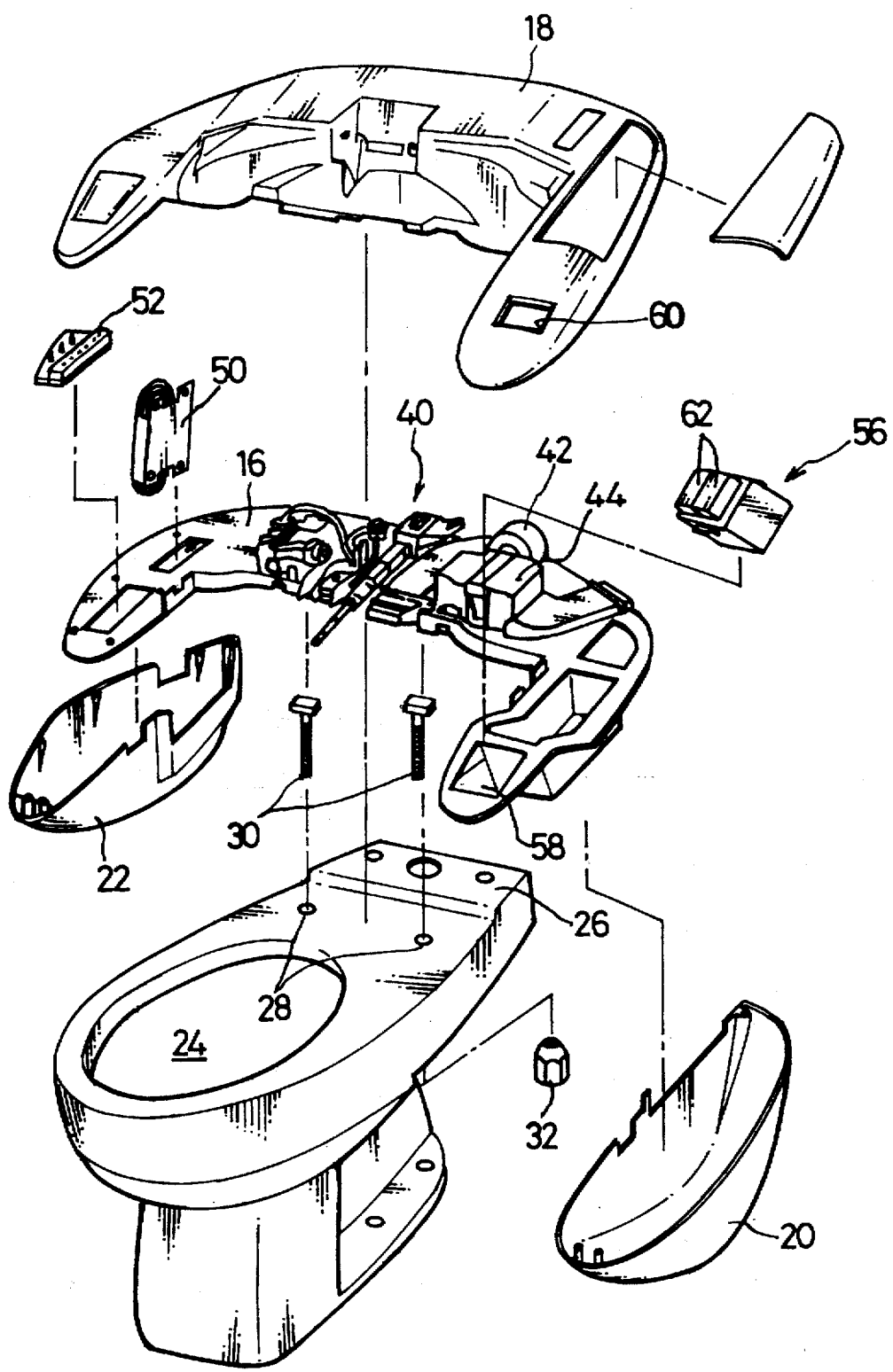
FIG. 2 is an exploded perspective view of the housing of the sphygmomanometer shown in FIG. 1.

The sphygmomanometer according to the first embodiment of the invention will now be described with reference to FIGS. 1–12. Referring to FIGS. 1 and 2, the toilet 10 is provided with a conventional water closet bowl fixture 12 to which a housing 14 is mounted. As best shown in FIG. 2, in the illustrated embodiment, the housing 14 comprises a frame 16, an upper casing 18 and a pair of lower casings 20 and 22, which are formed by injection molding of plastic material and are fastened together by screws and the like. Between a bowl section 24 and a cistern mounting section 26, the conventional bowl fixture 12 is provided with a pair of seat mounting holes 28 for use in mounting a toilet seat. The housing 14 is secured to the bowl fixture 12 by engaging a pair of T-bolts 30 into a pair of T-shaped slots formed on the underside of the frame 16 as described in Japanese Utility Model Kokoku Publication No. 63-6291 and by inserting the T-bolts 30 through respective seat mounting holes 28 followed by fastening associated nuts 32.

In the illustrated embodiment, the housing 14 has a central portion 34 extending transversely of the bowl fixture 12 and a pair of lateral portions 36 and 38 extending forwardly of the ends of the central portion. In this embodiment, the central portion 34 of the housing receives therein a conventional bidet system 40 having a spray nozzle, a conventional hot-air blower 42, and a conventional ventilation and deodorizer device 44. A toilet seat 46 and a toilet lid 48 are pivotally hinged to the housing central portion 34 in the well-known manner. A power source 50 and a control panel 52 for the bidet system 40 may be arranged within the right-hand lateral portion 38 of the housing.

The sphygmomanometer 54 according to the invention includes a measuring unit 56 which may be arranged on the left-hand lateral portion $6 of the housing. To this end, the frame 16 is provided with an opening 58 to permit installation of the measuring unit 56. Similarly, the upper casing 18 of the housing 14 is formed with an aperture 60 to permit the cuffs 62 of the measuring unit 56 to move therethrough. A control unit 64 for controlling the measuring unit 56 and for outputting the results of measurement may be installed, for example, on the side wall of the toilet as shown in FIG. 1. The control unit 64 may be provided with various operating switches as well as a liquid crystal display device and a printer for displaying and outputting the results of measurement and the trends of data.

Figure 3:
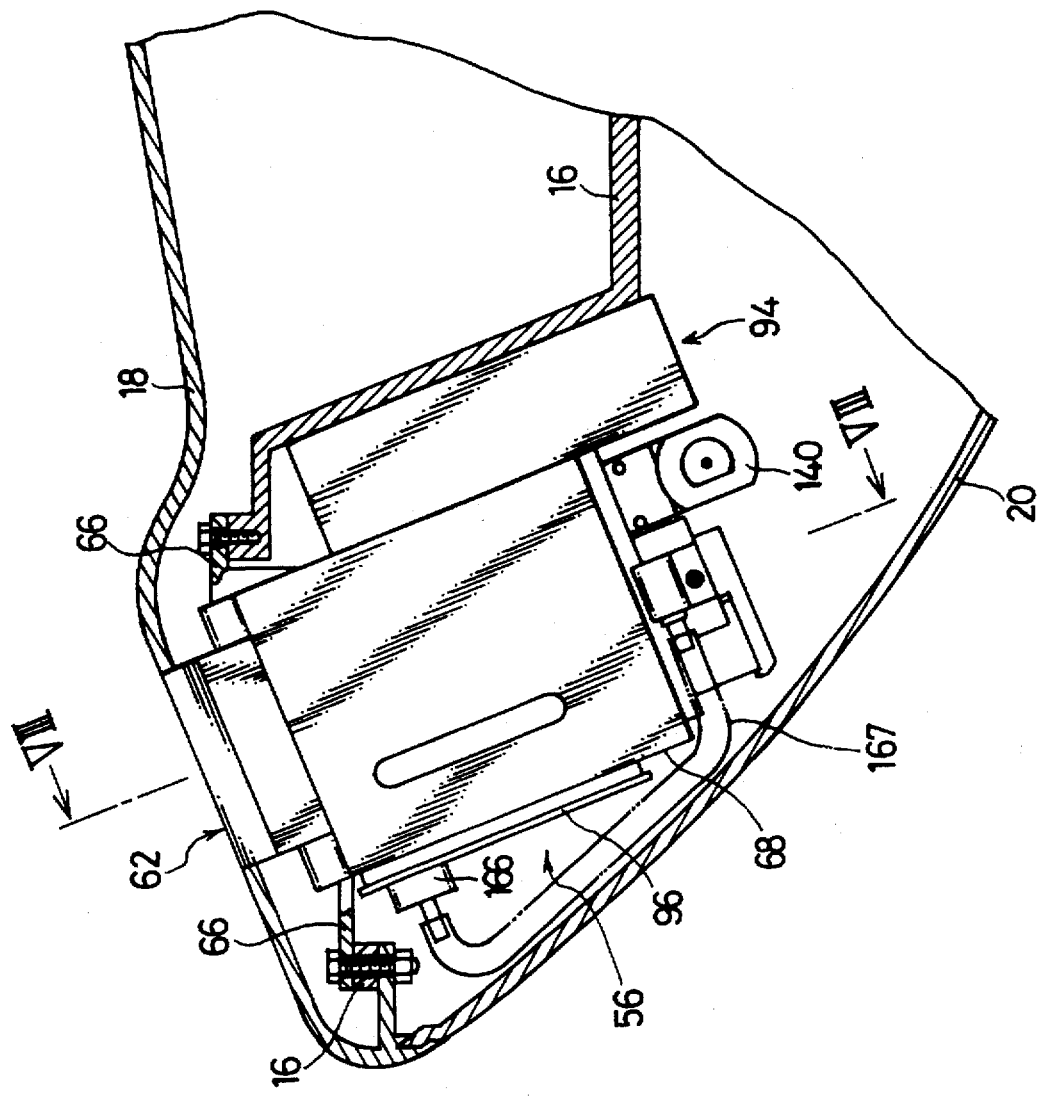
FIG. 3 is a cross-sectional view taken along the line III—III of FIG. 1.
Figure 4:
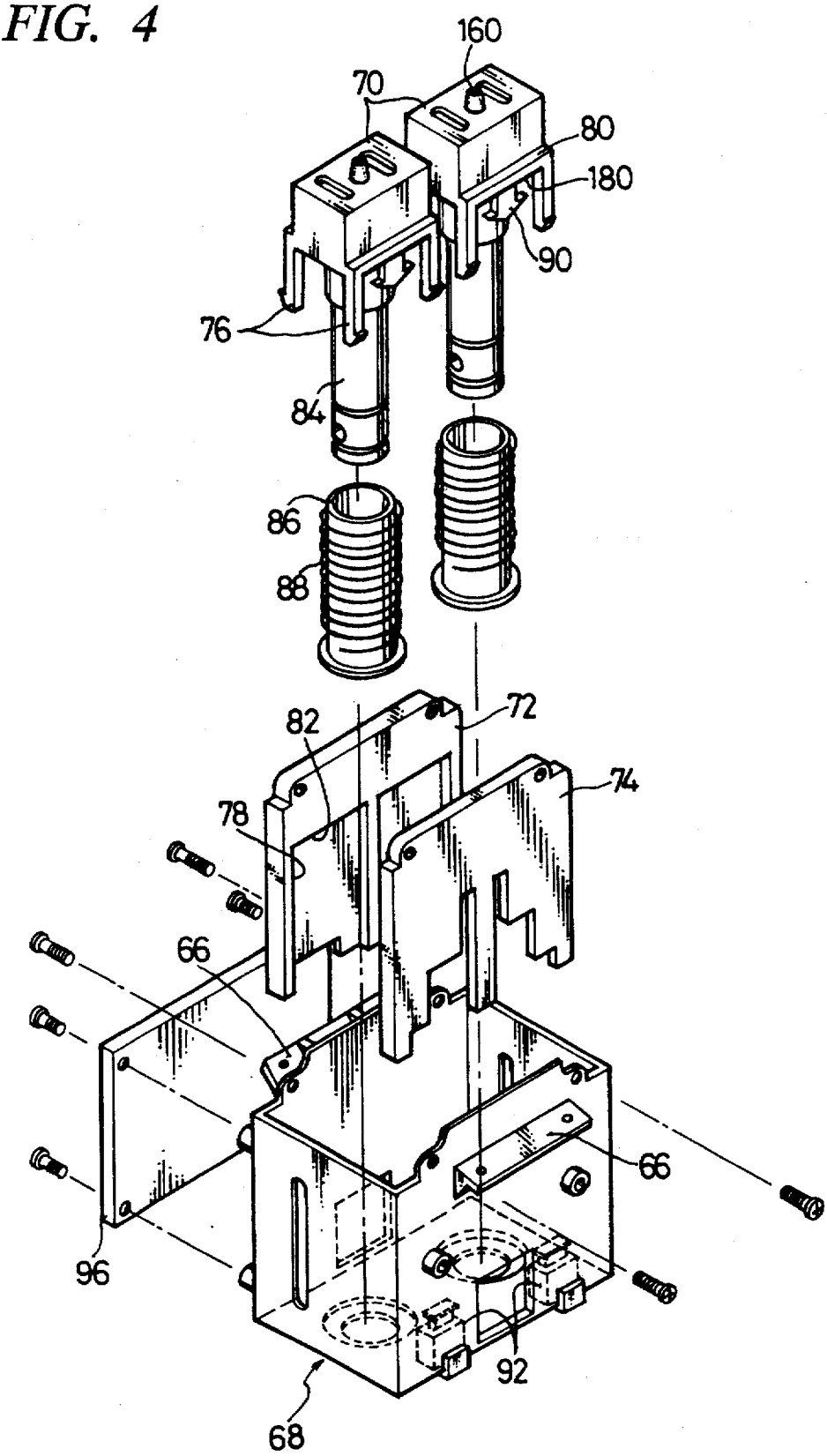
FIG. 4 is an exploded perspective view of a slider mechanism of the blood pressure measuring unit shown in FIGS. 2 and 3.

In the first embodiment, the measuring unit 56 is provided with a pair of large-sized and small-sized cuffs 62, each of which is adapted to be protracted and retracted through the aperture 60 of the housing by an associated slider mechanism. Referring to FIGS. 3 and 4, the measuring unit 56 has a casing 68 with a mounting flange 66 and is secured to the frame 16 of the housing 14 by screws and the like. As shown in FIG. 4, the casing 68 slidably receives a pair of sliders 70 to which the cuffs 62 are secured, respectively. In the illustrated embodiment, a pair of guide plates 72 and 74 serving as guide rails for the sliders 70 are fixed by screws to the casing 68 to guide respective sliders 70 for sliding movement and to limit the stroke thereof. To this end, each of the guide plates 72 and 74 is formed with a shallow recess 78 adapted to guide four resilient legs 76 of the associated slider 70. Further, each of the sliders 70 is provided with a shoulder 80 which is adapted to abut against the upper edge 82 of the recess 78 to dictate the stroke of the slider 70.

Each slider 70 has a downwardly extending plunger 84 formed, for example, by integral molding, the plunger 84 being adapted to move up and down within a spring guide 86. A coiled spring 88 is arranged around the spring guide 86 to upwardly bias the associated slider 70.

Each slider 70 is designed such that upon depressing the cuff 62 the associated slider is latched in the retracted position but upon depressing the cuff 62 once again the slider is unlatched thereby to allow the cuff 62 to project out of the housing 14 under the action of the coiled spring 88. To this end, push-and-return latch mechanisms marketed by K.K. Nifco under the trademark "Floating Latch" are used, with each slider 70 being provided with a striker 90 of the latch mechanism and with an associated bush 92 for latching the striker 90 being arranged on the bottom of the casing 68. Such latch mechanisms are well-known and need not be described in any detail. As shown in FIG. 3, an interlock mechanism 94 is arranged at the back of the casing 68 to prevent the two cuffs 62 from being projected simultaneously. This interlock mechanism 94 will be described later with reference to FIGS. 9–11. Secured to the front part of the casing 68 is a circuit board 96 on which a control and processing circuit, described later, for the measuring unit 56 is mounted.

Figure 5:
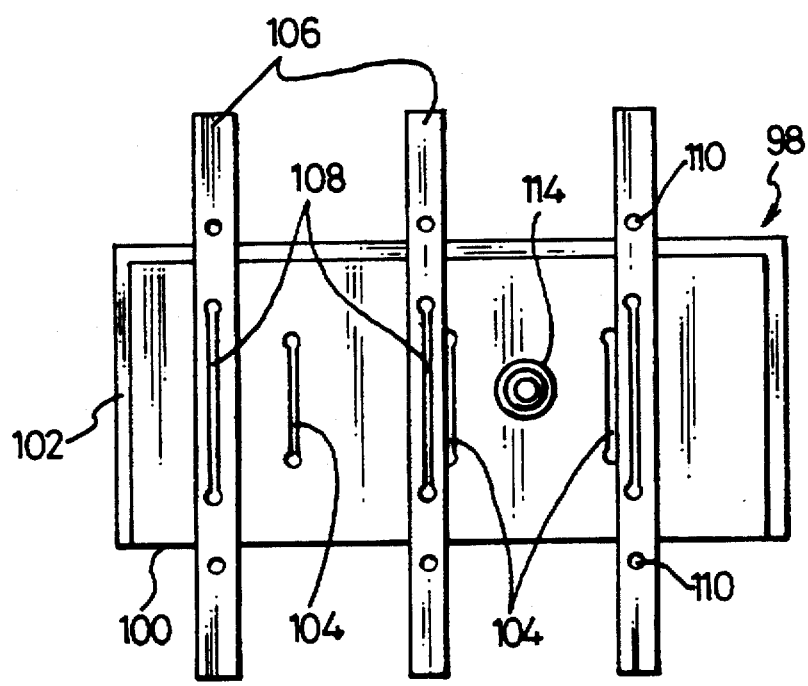
FIG. 5 is a developed view showing an example of the bladder of the occluding finger cuff.
Figure 6:
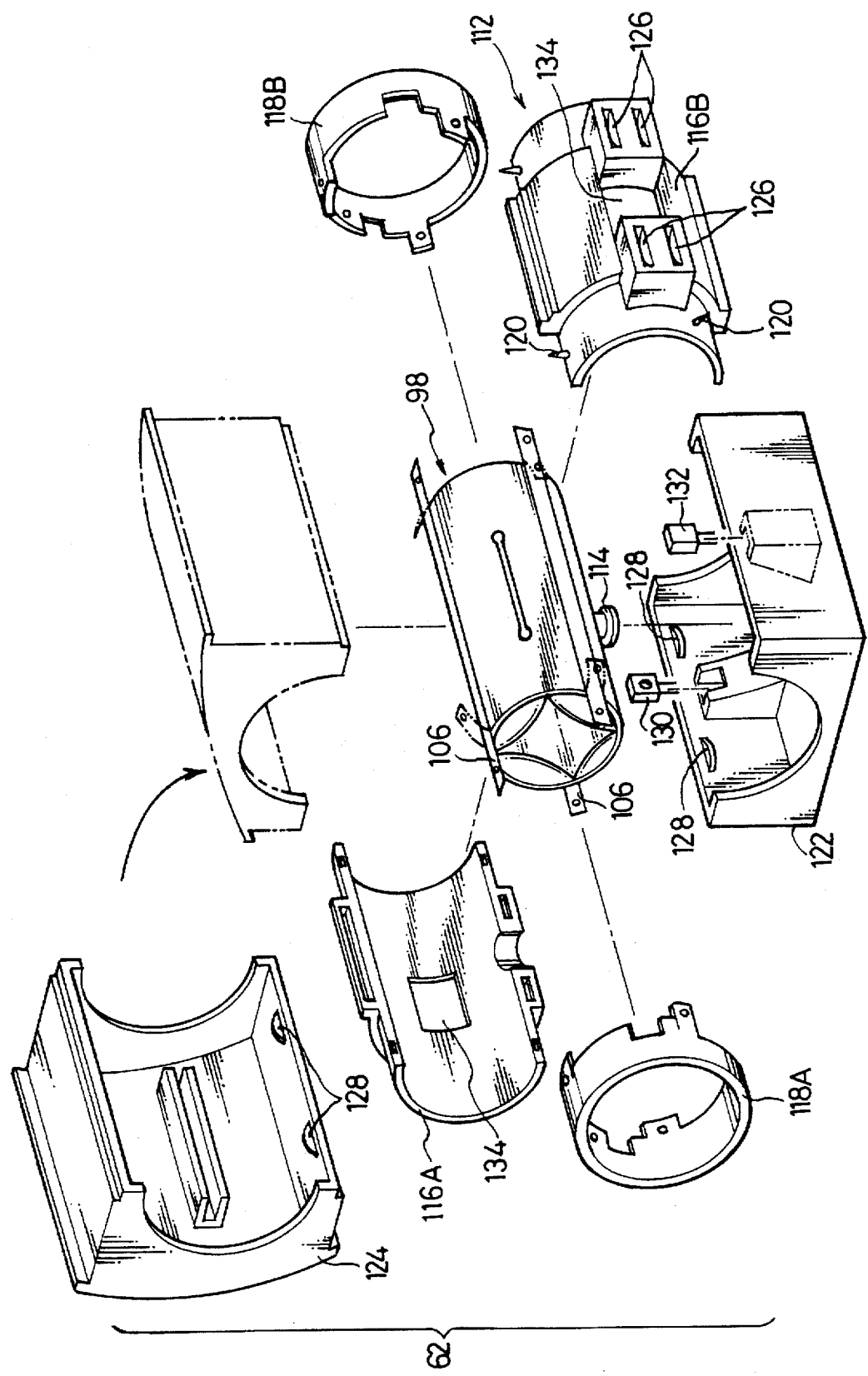
FIG. 6 is an exploded perspective view of the cuff shown in FIG. 3.

Referring to FIGS. 5 and 6, the cuffs 56 of the measuring unit 56 will be described. The two cuffs 62 are generally identical with one another and the primary difference resides only in size. Therefore, only one of the cuffs will be described. Referring to FIG. 5, the cuff 62 has a bladder 98 which may be made of a rectangular sheet of polyurethane by folding the sheet over along a fold line 100 and by heat sealing the outer and inner sheets along the three sides 102 by high frequency welding. The outer and inner sheets are further welded with each other along three welding seams 104, for example. Three flexible fixing bands 106 made of polyurethane strip are bonded along welding seams 108 to the outer sheet of the bladder 98. Each band 106 is provided with a pair of apertures 110 in order to detachably fix the bladder 98 to a casing 112 of the cuff 62, the casing 112 being made of rigid material such as hard plastics. Welded also to the outer sheet of the bladder 98 is an air joint 114 to which a hose extending from an air pump, described later, is connected so as to distend the bladder 98 thereby to compress and occlude the finger of the user upon application of air under pressure.

Referring to FIG. 6, the casing 112 of the cuff 62 is comprised of a pair of casing halves 116A and 116B in the form of split tube and of a pair of fastening rings 118A and 118B arranged at the ends of the casing halves. Each of the casing halves is provided with a plurality of projections 120 corresponding to the apertures 110 of the fixing bands 106. The casing 112 is assembled and the bladder 98 removeably secured to the casing by bending the ends of the fixing bands 106 as shown by the ghost line in FIG. 6, by engaging the apertures 110 of the bands 106 over the projections 120 and by mating the two casing halves with each other, followed by snap fitting the fastening rings 118 over the ends of the casing halves.

The assembly of the casing 112 and the bladder 98 thus assembled is then fixed in a releasable manner to the slider 70 by means of a cuff base 122 and a cover 124. To this end, the casing halves 116A and 116B are provided at the sides thereof with notches 126 and the cuff base 122 and the cover 124 are provided with projections 128 engageable with these notches. When an excessive force is applied to the cuff 62 such as the case where the user abruptly stands up while the finger is inserted into the cuff 62, the projections 128 will be readily disengaged from the notches 126 thereby preventing the finger and the cuff 62 from being inadvertently injured or damaged. The respective cuffs 62 are secured to the associated sliders 70 by fixing the cuff bases 122 to the sliders 70 by screws and the like.

Each of the cuff bases 122 is provided with a light emitting element 130 such as a near infrared light emitting diode and a photosensor 132 such as a phototransistor, the casing halves 116 being provided with light transmitting windows 134. The light emitting element 130 is energized as air under pressure is supplied to distend the bladder 98 to compress the artery of the user's finger, preferably the second finger, inserted into the cuff 62. The light from the light emitting element 130 is irradiated on the finger through the bladder 98 made of an opaque polyurethane sheet, the transmitted light being detected by the photosensor 132. The signal from the photosensor is delivered to a photoelectric plethysmograph, described later with reference to FIG. 12, mounted on the circuit board 96 whereby the artery blood pressure is detected by way of the conventional volume oscillometric method. The results are transmitted via cable communication to the control unit 64 for visual display and/or output.

Figure 7:
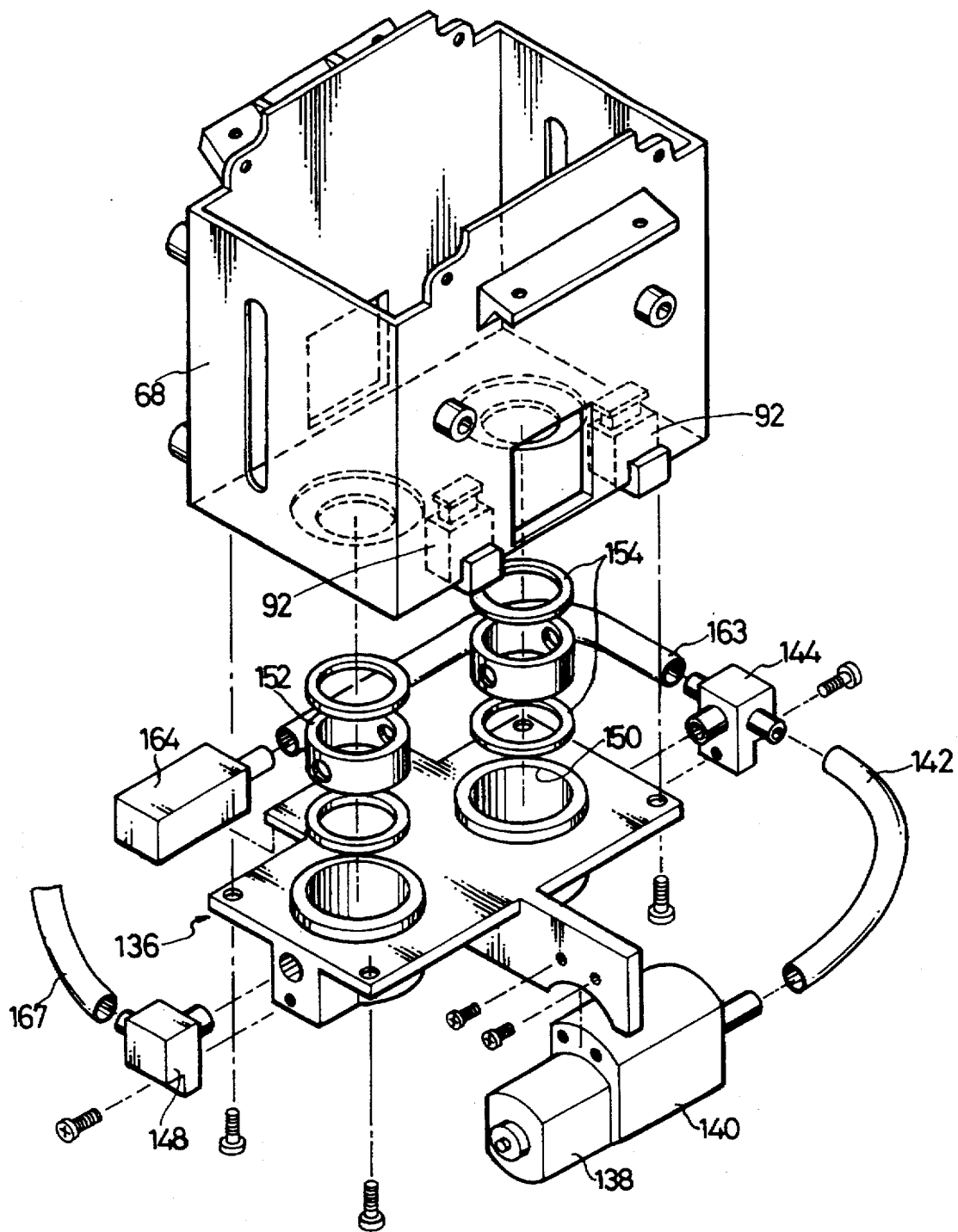
FIG. 7 is an exploded perspective view of the air supply system of the measuring unit shown in FIGS. 2 and 3.
Figure 8:
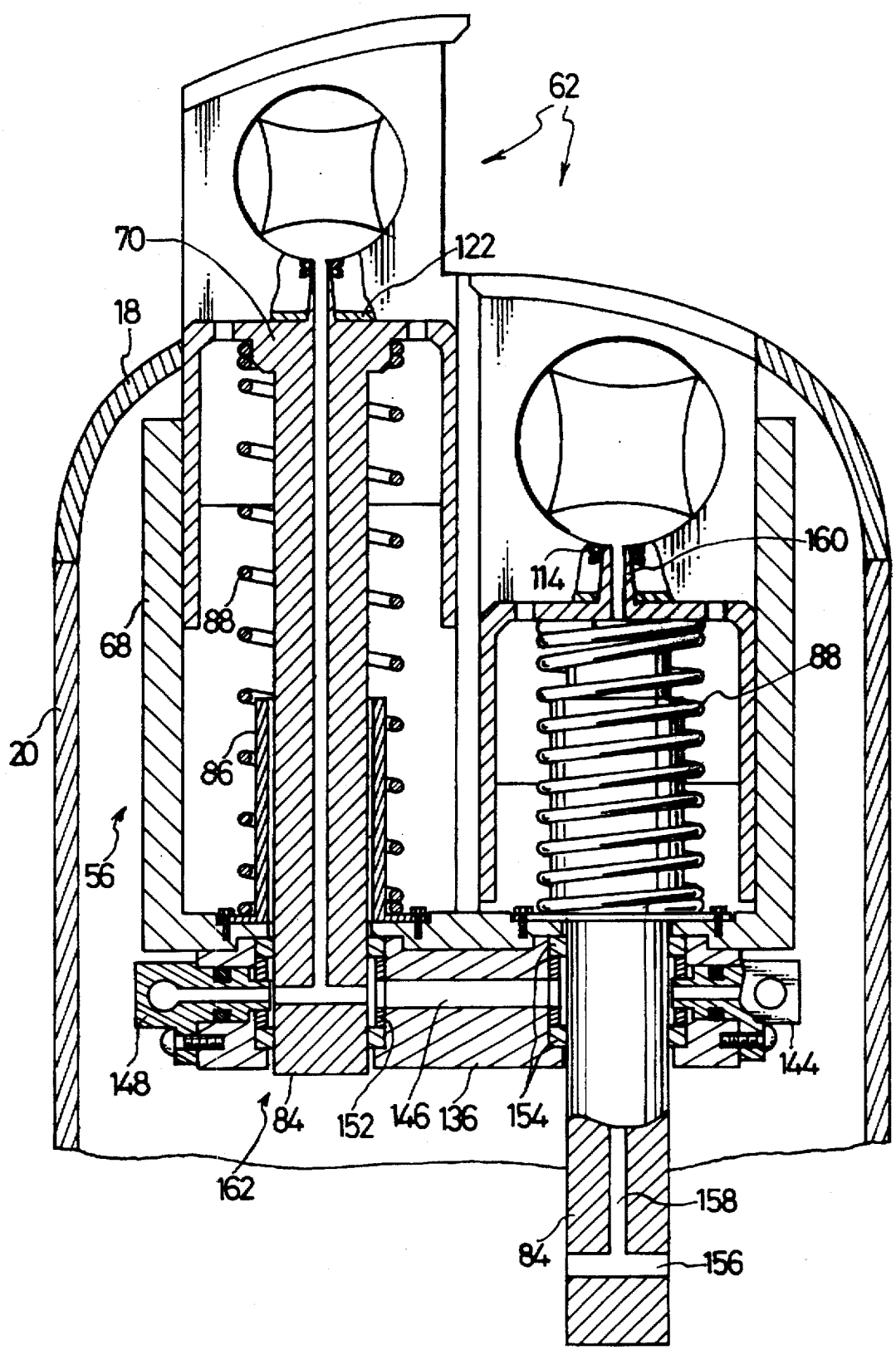
FIG. 8 is a cross-sectional view taken along the line VIII—VIII of FIG. 3 and showing a cuff protruded from the housing and another cuff retracted within the housing.

Referring next to FIGS. 7 and 8, the air supply system for supplying air under pressure to the bladder 98 will be described. Secured by screws to the underside of the casing 68 is a valve case 136 on which is mounted an air pump 140 such as a swash-plate type diaphragm pump driven by a motor 138. Air under pressure from the air pump 140 is delivered through a hose 142 to a T-joint 144. The valve case 136 has a longitudinally extending air passage 146 connected at an end to the T-joint 144, the other end of the passage 146 being connected to an elbow 148. The valve case 136 is formed with a pair of bores 150 coaxial with the plungers 84 of respective sliders 70 and a pair of Y-packing spaced apart by a collar 152 are fitted in each bore 150. As best shown in FIG. 8, each plunger 84 is provided with a transverse air passage 156 parallel to the air passage 146 of the valve case 136 and an axial air passage 158 in communication with the transverse air passage 156 and extending axially of the plunger 84, the axial air passage 158 being in communication with a nipple 160 formed at the top of the slider 70 for engagement with the air joint 114 of the bladder 98. The plunger 84 and the valve case 136 cooperate together to form a shut-off valve 162 that controls the supply of air under pressure to the bladder 98 of the cuff 62 in response to the sliding movement of respective sliders 70. To this end, the transverse air passage 156 of each plunger 84 is designed to be aligned with the air passage 146 of the valve case 136 when the associated slider 70 is lifted.

With this arrangement, upon bringing the cuff 62 to protract as shown in the left part of FIG. 8, air under pressure form the air pump 140 will be supplied to the bladder 98 of the corresponding cuff 62 thereby causing the bladder to distend, and upon retracting the cuff 62 as shown in the right part of FIG. 8, air supply will be interrupted. In the illustrated embodiment, the two cuffs 62 has an inner diameter of 23 mm and 27 mm, respectively, the aspect ratio (the ratio of the length L to the diameter D) of both cuffs being selected to be L/D≈1.2 in conformity with the recommendations of the American Heart Association. A person like a male having a large finger may use the large diameter cuff whereas a female or child may select the small diameter cuff.

The T-joint 144 is also connected through a hose 163 to a solenoid-operated discharge valve 164 to release the pressure of the cuffs 62. The elbow 148 is, in turn, connected through a hose 167 to a pressure sensor 166 (FIG. 3) secured to the circuit board 96 so as to detect the cuff pressure.

Figure 9:
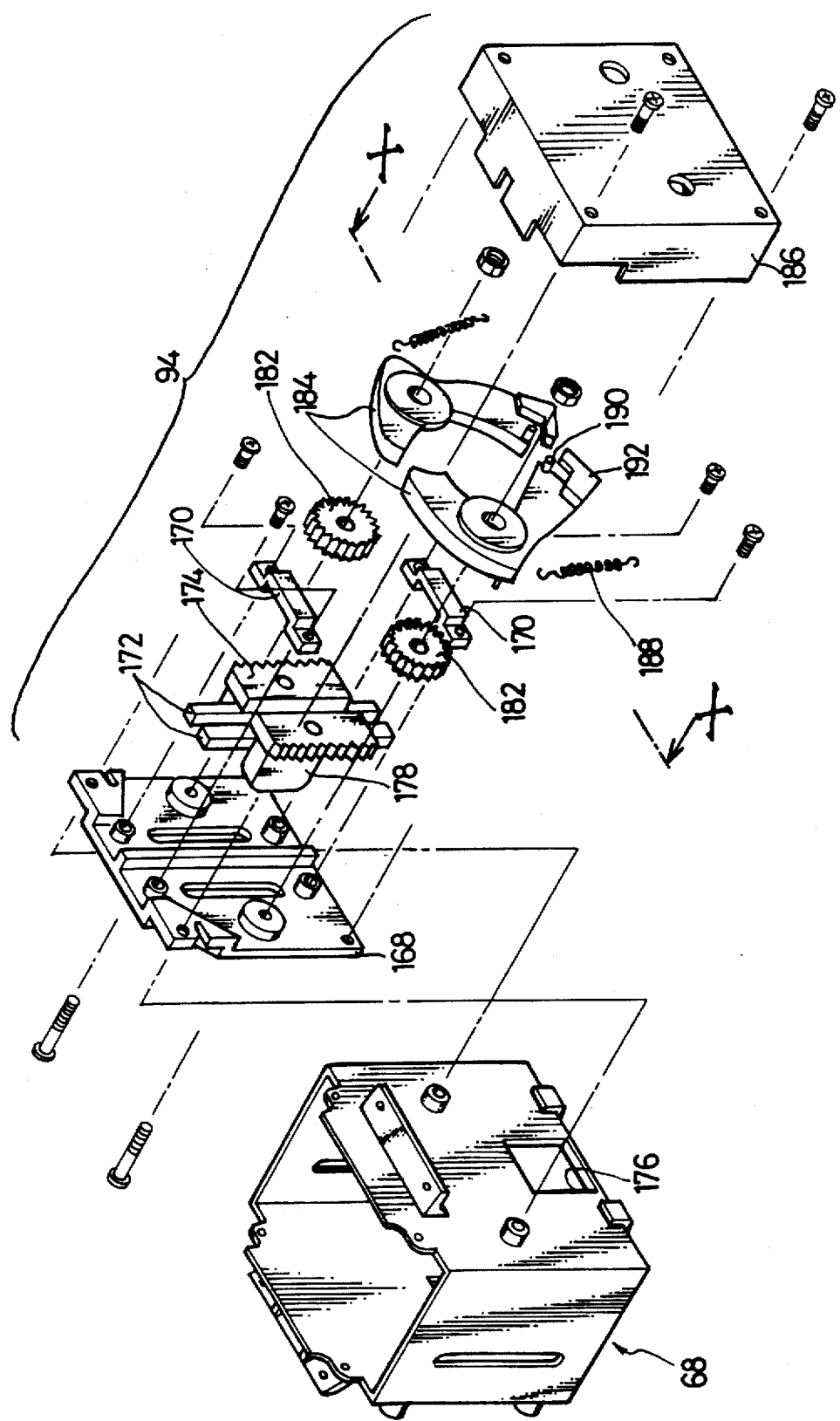
FIG. 9 is an exploded perspective view of the interlock mechanism of the measuring unit shown in FIGS. 2 and 3.
Figure 10:
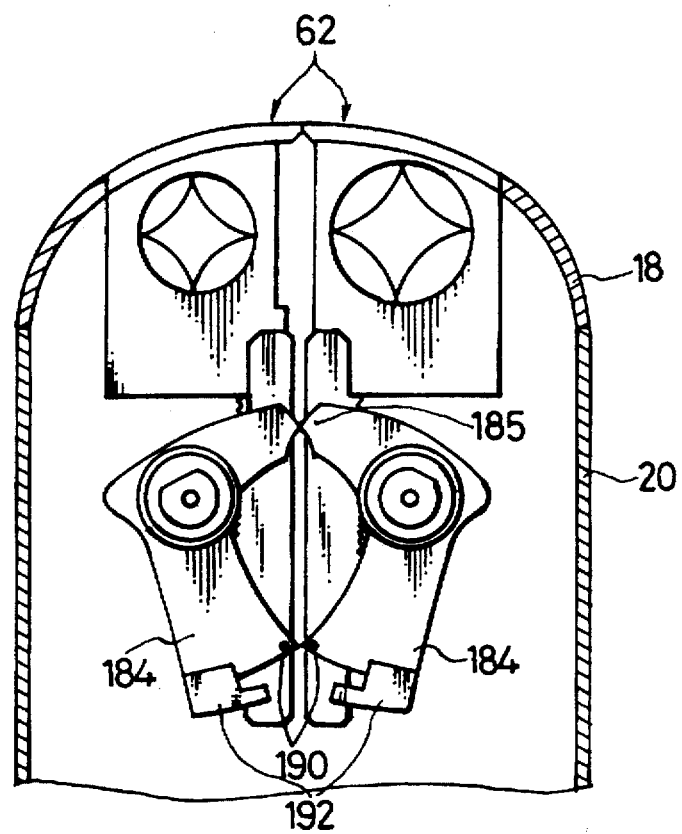
FIG. 10 is a cross-sectional view taken along the line X—X of FIG. 9 and showing all the cuff being in their retracted position.

The interlock mechanism 94 will be described with reference to FIGS. 9–11. A base plate 168 is bolted to the casing 68 of the measuring unit 56 and a pair of rack assemblies 172 is mounted slidably to the base plate 168 by means of a pair of vertically spaced brackets 170. Each rack assembly 172 has a rack 174 secured thereto. Secured also to each rack assembly 172 is a projection 178 projecting inwardly of the casing 68 through a window 178 in the casing 68 in such a manner that a lower edge 180 (FIG. 4) of the shoulder 80 of the slider 70 is brought into engagement with the projection 178 as the slider 70 is depressed down into the casing 68.

A pair of pinions 182 in mesh with the respective racks 174 and a pair of interlock levers 184 adapted to swing integrally with these pinions are pivoted to the base plate 168 and are protected by a cover 186. Since the pinions 182 rotate conjointly with respective interlock levers 184, the latter will be rotated as the racks 174 move up and down. The interlock levers 184 are biased in opposite directions by respective return springs 188. Each of the interlock levers 184 is provided at its lower end with a pin 190 and a hook 192 adapted to engage with the pin 190 of the opposite interlock lever.

As described before, the latch mechanism 90/92 (FIG. 4) of each slider 70 is of the push-and-return type so that, once the slider 70 has been latched, it would not be unlatched unless the cuff 62 is first depressed. As long as both of the two cuffs 62 are in the retracted position as shown in FIG. 10 and, therefore, are latched by respective push-and-return latching mechanisms 90/92, the upper ends 185 of the two interlock levers 184 abut against with each other thereby precluding the two levers 184 from being rotated simultaneously. Accordingly, even though both of the two cuffs 62 are depressed at a time, neither of the sliders 70 will be released.

Figure 11:
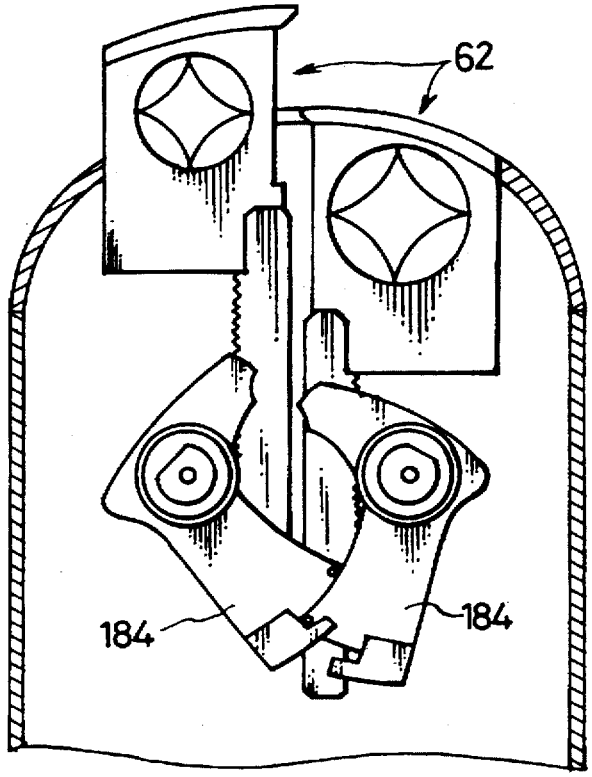
FIG. 11 is a cross-sectional view similar to FIG. 10 but showing one of the cuffs in the protracted position.

When either of the cuffs 62 is depressed, the corresponding interlock lever 184 will be rotated as shown in FIG. 11 thereby allowing the associated latching mechanism 90/92 to be unlatched whereby the slider 70 is released and is lifted under the action of the coiled spring 88 causing the depressed cuff 62 to protrude upwards out of the upper surface of the upper casing 18 of the housing. In this condition, the user is able to insert the finger into the projected cuff 62 to measure the artery blood pressure. Also, in this state, it is impossible to try to depress and protrude the another cuff 62 because the other interlock lever 184 is blocked by the opposite interlock lever 184 as shown in FIG. 11. When after blood pressure measurement the used cuff 62 is depressed again, the corresponding slider 70 will be latched by the associated latching mechanism 90/92 and both of the cuffs will be retracted within the lateral portion 36 of the housing as shown in FIGS. 1 and 10.

Figure 12:
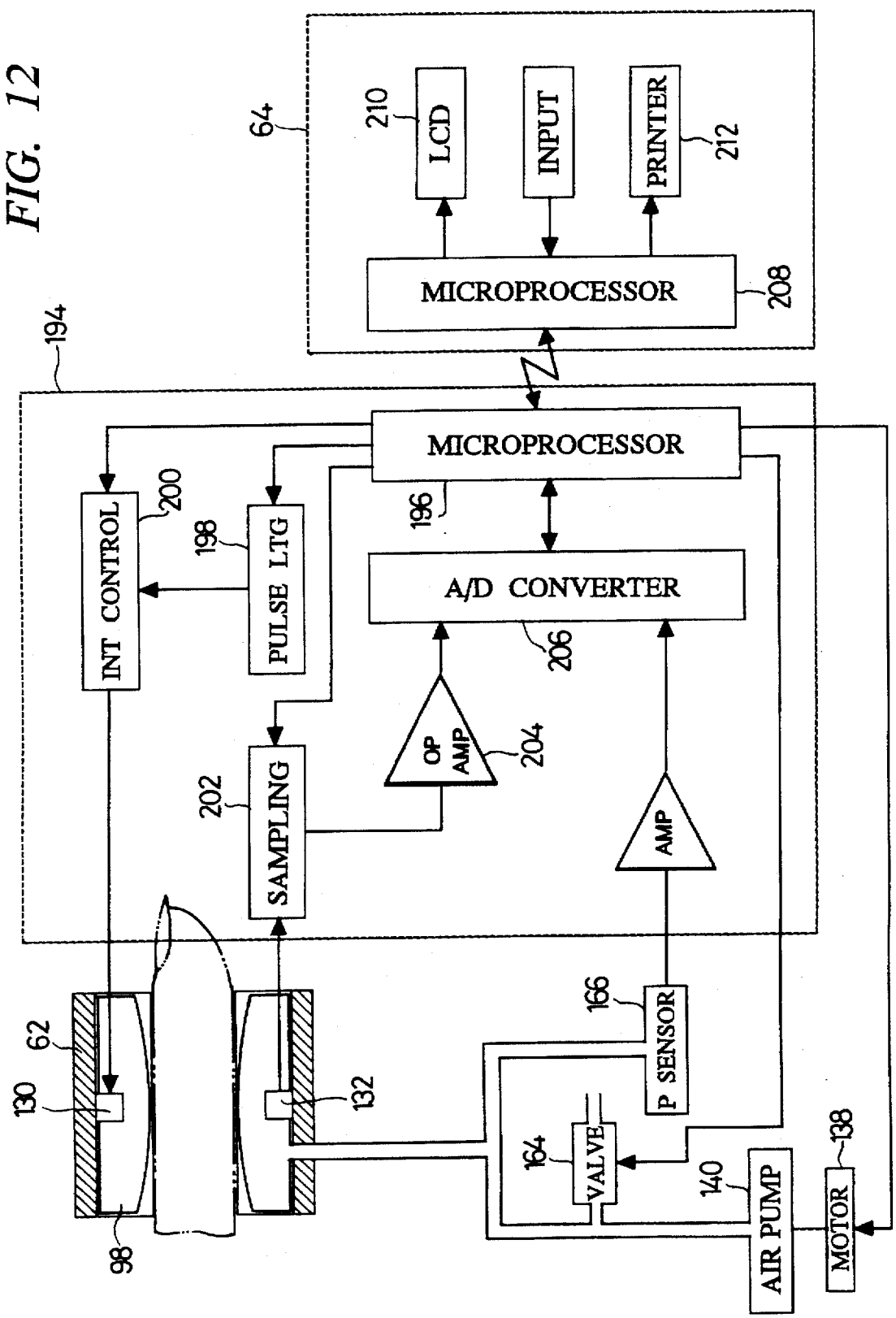
FIG. 12 is a block diagram showing the electric circuitry of the sphygmomanometer shown in FIG. 1.

In FIG. 12, there is shown, byway of an example, a layout of the control and processing circuit 194 mounted to the circuit board 96 of the measuring unit 56 and the control unit 64 mounted on the toilet wall. The control and processing circuit 194 is of the conventional one and includes a programmed microprocessor 196. As the user engages its finger into the cuff and presses on a start switch of the control unit 64, the microprocessor 196 operates to drive the motor 138 of the air pump 140 to distend the compression bladder 98 of the cuff 62. The microprocessor 196 also signals a pulse lighting circuit 198 and a light intensity control circuit 200 to cyclically energize the near-infrared light emitting diode 1S0 to operate with a controlled light intensity. The near infrared light transmitted across the finger is detected by the phototransistor 1S2 and the output thereof is cyclically sampled by a sampling circuit 202, the output being amplified by an operational amplifier 204 and delivered to an analog-to-digital (A/D) converter 206. The microprocessor 196 monitors the signal from the A/D converter 206 and detects the plethysmogram of the finger artery in the conventional manner.

Upon detecting that the finger artery of the user is occluded in response to distention of the bladder 98, the microprocessor 196 signals the solenoid-operated discharge valve 164 to open thereby to slowly discharge air in the bladder 98. During slow discharge, the microprocessor 196 monitors the plethysmogram and computes the blood pressure and pulse rate in accordance with the conventional volume oscillometric method. Alternatively, the microprocessor 196 may be so programmed that the blood pressure and pulse rate are detected as the cuff pressure is increased and that the cuff pressure is rapidly released upon completion of measurement. The results of the measurement are transmitted by data communication through a communication cable, not shown, to a microprocessor 208 of the control unit 56 which, in turn, displays the results on a liquid crystal display panel 210 or signals a printer 212 to output the results in response to the instructions of the user.

Figure 13:
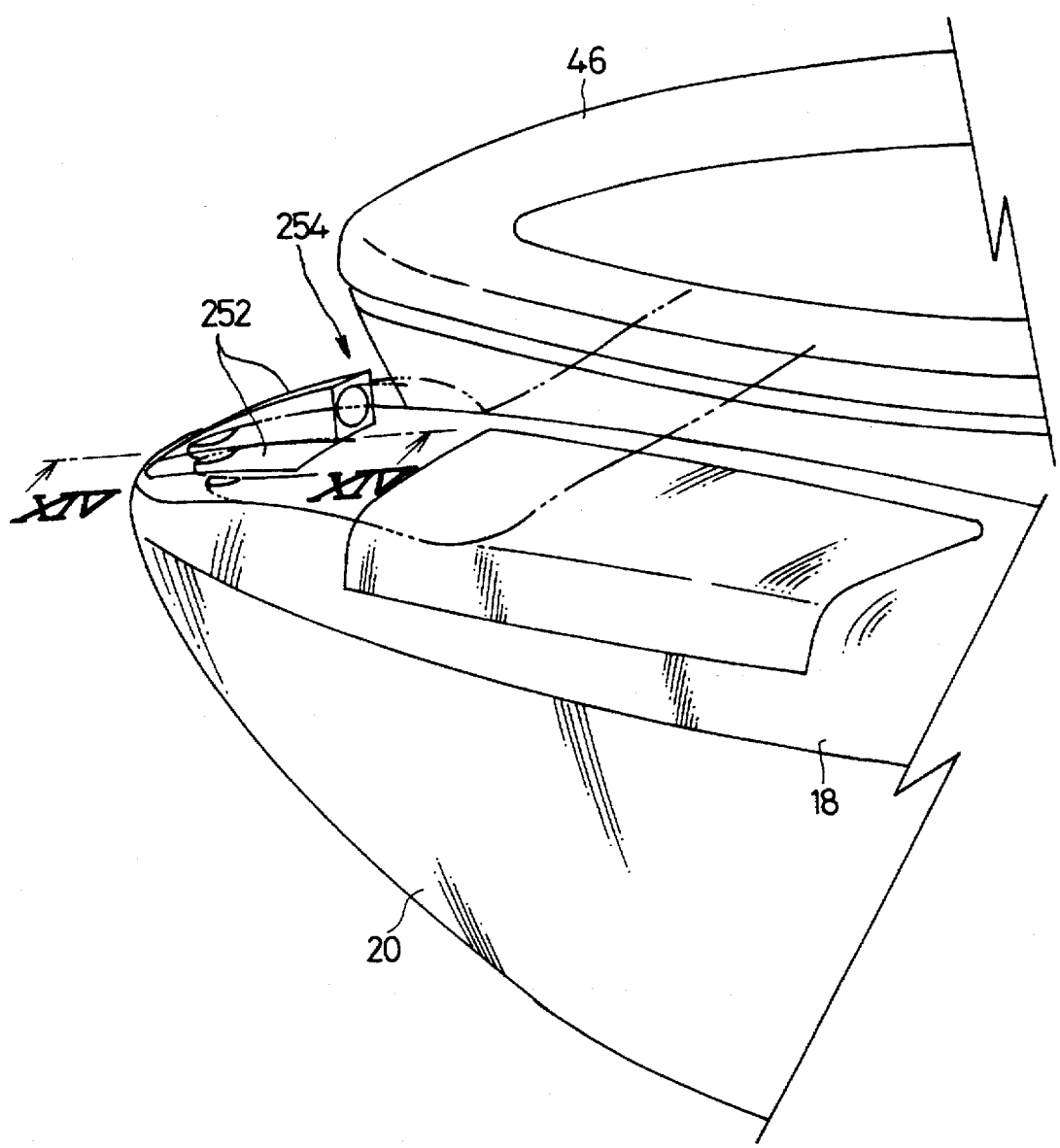
FIG. 13 is a perspective view of the sphygmomanometer according to the second embodiment of the invention and showing one of the pivoting arms being pulled up for engagement by a finger of the user.
Figure 14:
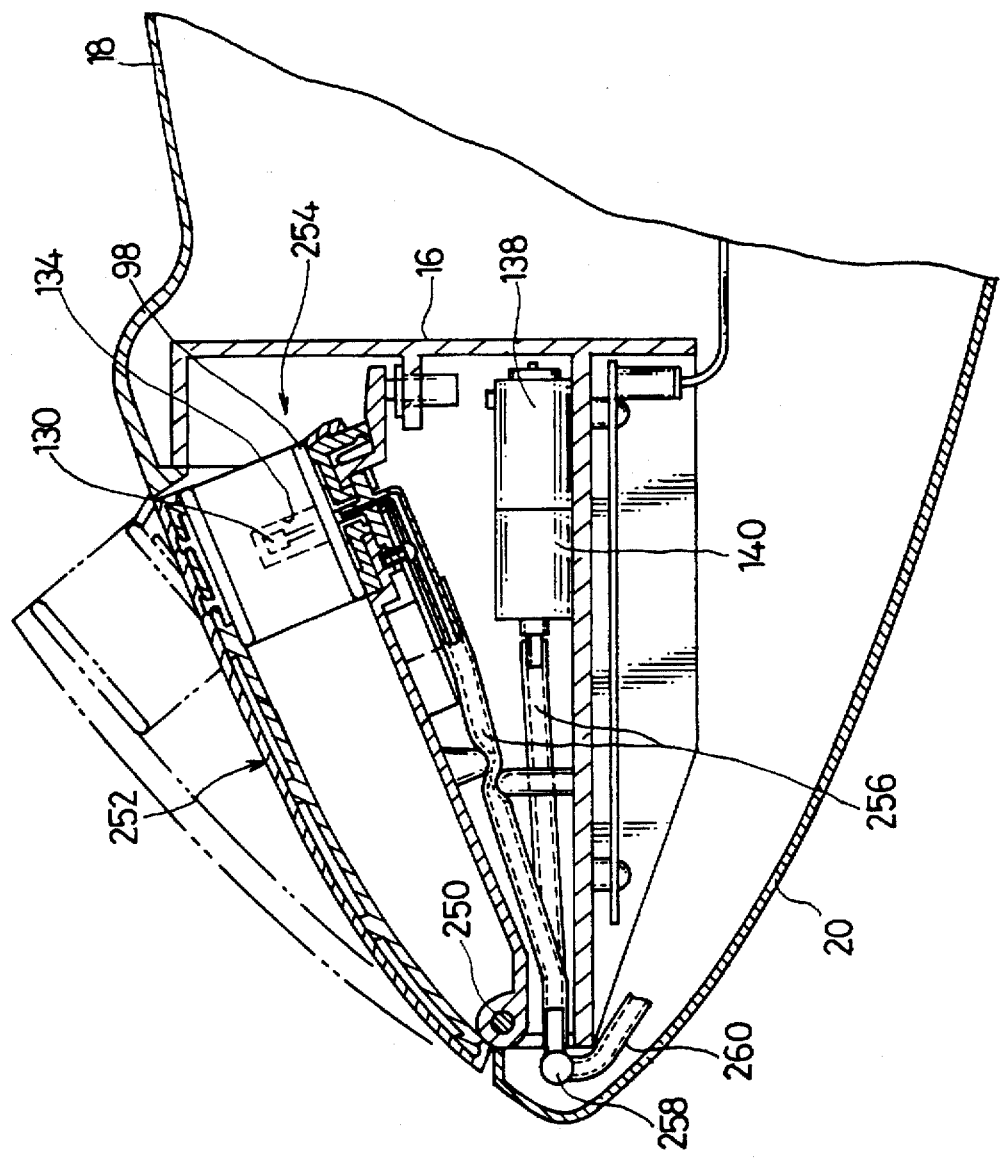
FIG. 14 is a cross-sectional view taken along the line XIV—XIV of FIG. 13.

In FIGS. 13 and 14, there is shown the digital sphygmomanometer according to the second embodiment of the invention. Parts and members similar to those of the foregoing embodiment are indicated in these drawings by like reference numerals and, therefore, will not be described again. In this embodiment, a pair of parallel pivoting arms 252 are hinged at the forward end thereof to the frame 16 of the housing by way of a pivot 250 and a pair of cuffs 254 each having the bladder 98 are mounted to the rear end of respective arms 252. Air under pressure is supplied to respective cuffs 254 from the air pump 140 through hoses 256, the cuff pressure being communicated to the pressure sensor, not shown, through a hose 260 connected to a branch joint 258.

Similar to the first embodiment, the two cuffs 254 are different in size to accommodate fingers of different diameter. The user may select at its option a cuff of an appropriate size meeting with the diameter of its own finger by rotating either of the pivoting arms 252 so as to lift the selected cuff as shown by the solid line in FIG. 13 and by the ghost line in FIG. 14 and then commence the blood pressure measurement by inserting the finger therein as shown in FIG. 13.

In FIGS. 15–18, there is shown the digital sphygmomanometer according to the third embodiment of the invention. The feature of this embodiment is that a pair of cuff different in size are mounted to a revolving member. In these drawings, parts and members similar to those of the first embodiment are indicated in these drawings by like reference numerals and will not be described again. Referring to FIGS. 15–18, a pair of supports 300 and 302 are bolted to the frame 16 of the housing 14 and a pair of trunnions 306 and 308 of the revolving member 304 are journaled, respectively, to these supports.

The revolving member 304 has a generally triangular cross-section and presents three outer surfaces 310, 312 and 314. In order to lock the revolving member 304 at such angular positions in which respective outer surfaces are selectively brought into registration with the aperture 60 of the upper housing 18, a ball 318 biased by a spring 316 is arranged in the front support 300 and three hemispherical notches 320 engageable with the ball are correspondingly formed on the end face of the revolving member 304.

A large-diameter cuff 322 and a small-diameter cuff 324 are mounted, respectively, on the outer surfaces 312 and 314 of the revolving member 304. As both cuffs are mounted in a similar manner, only the cuff 322 will be described. The outer surface 312 is formed with a shallow groove 326 which is configured to accommodate the base of the cuff 322. The cuff 322 is releasably mounted to the revolving member 304 by four spring-biased balls 328 (only two of such balls appearing in FIG. 17) engaging with associated four hemispherical notches 330 (similarly, only two of the notches being shown) in such a manner that the cuff is dismounted from the revolving member 304 when subjected to an excessive force.

Figure 17:
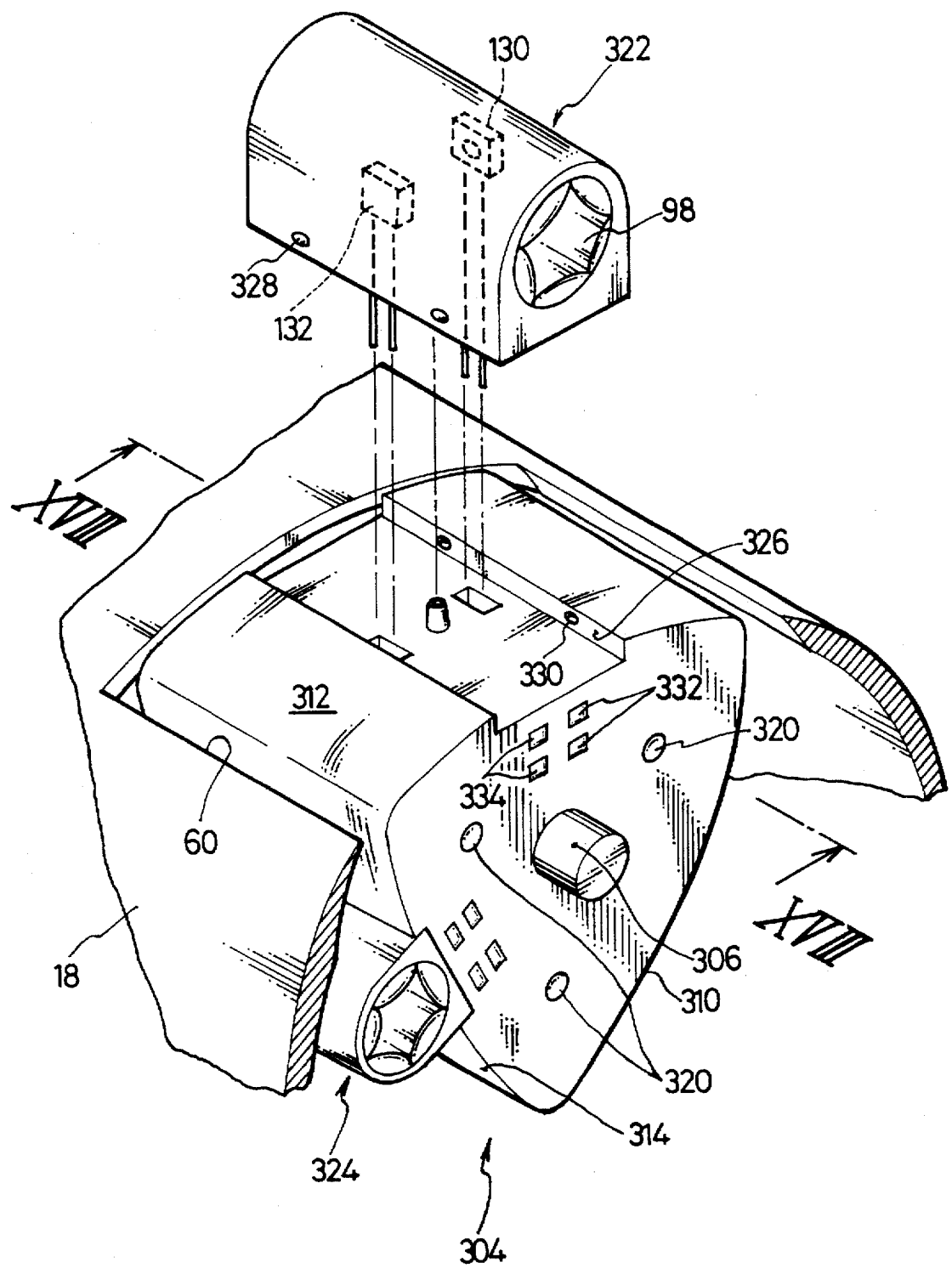
FIG. 17 is a cross-sectional view taken along the line XVII—XVII of FIG. 15 and showing one of the cuffs being dismounted from the revolving member.
Figure 18:
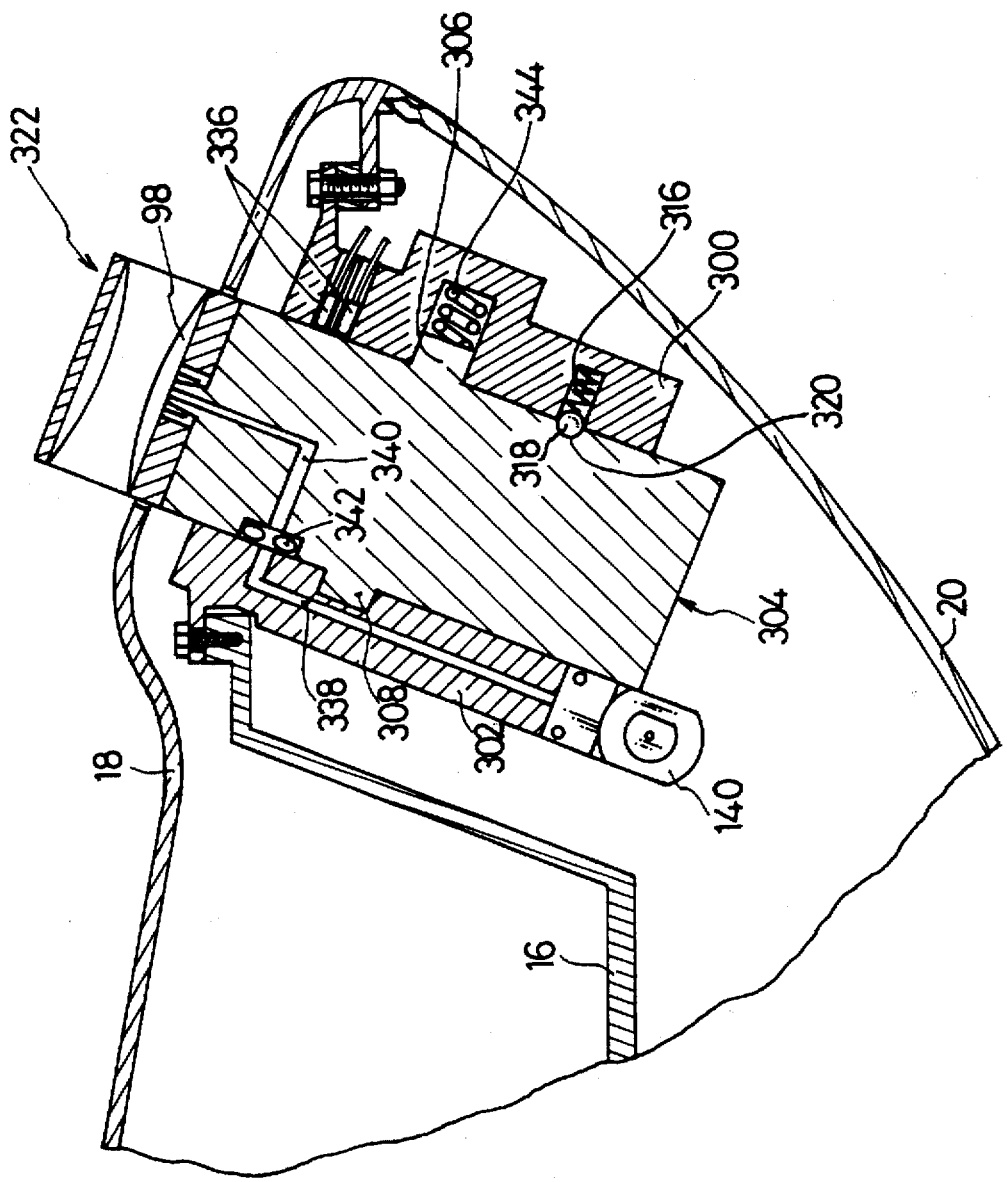
FIG. 18 a cross-sectional view taken along the line XVIII—XVIII of FIG. 17.

As will be readily understood from FIG. 17, the leadwires from the light emitting diode 130 and the phototransistor 132 extend through the revolving member 304 and are connected to respective pairs of terminals 332 and 334 arranged on the end face of the revolving member 304. As shown in FIG. 18, the front support 300 is provided with two pairs of fixed contacts 336 in such a manner as to be brought into contact with each pair of terminals 332 and 334 as the revolving member 304 is rotated at a predetermined angular position.

Air under pressure is supplied from the air pump 140 to the bladder 98 of the cuff 322 through a passage 338 formed in the rear support 302 and a passage 340 formed in the revolving member 304. A sealing member 342 such as an O-ring is arranged at the rear end face of the revolving member 304 to air tightly connect the passages 338 and 340 with each other. The revolving member 304 is biased rearwardly by a spring 344 to sealingly compress the sealing member 342.

Figure 15:
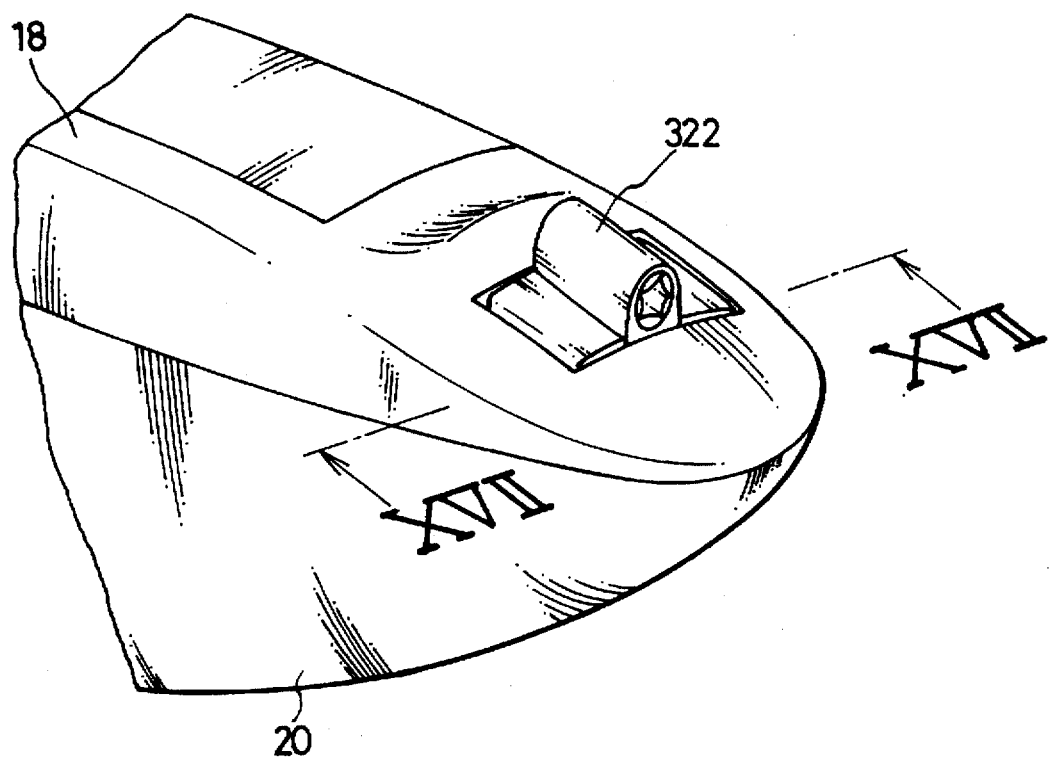
FIGS. 15 and 16 are perspective views of the sphygmomanometer according to the third embodiment of the invention and showing, respectively, the cuff as emerged from and retracted within the housing by rotating the revolving member.
Figure 16:
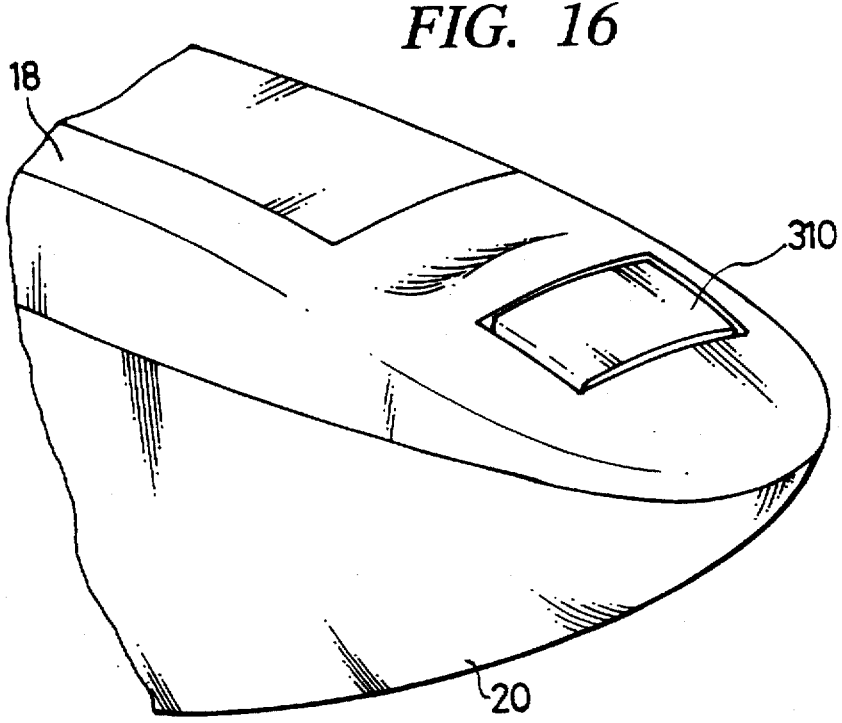

When not in use, the revolving member 304 may be positioned at such an angular position in which the outer surface 310 not provided with the cuffs is exposed as shown in FIG. 16. For blood pressure measurement, the user may rotate the revolving member 304 until a cuff of an appropriate size meeting with the diameter of the user's finger is emerged out of the housing as shown in FIG. 15 thereby to permit use of the selected cuff.

Figure 19:
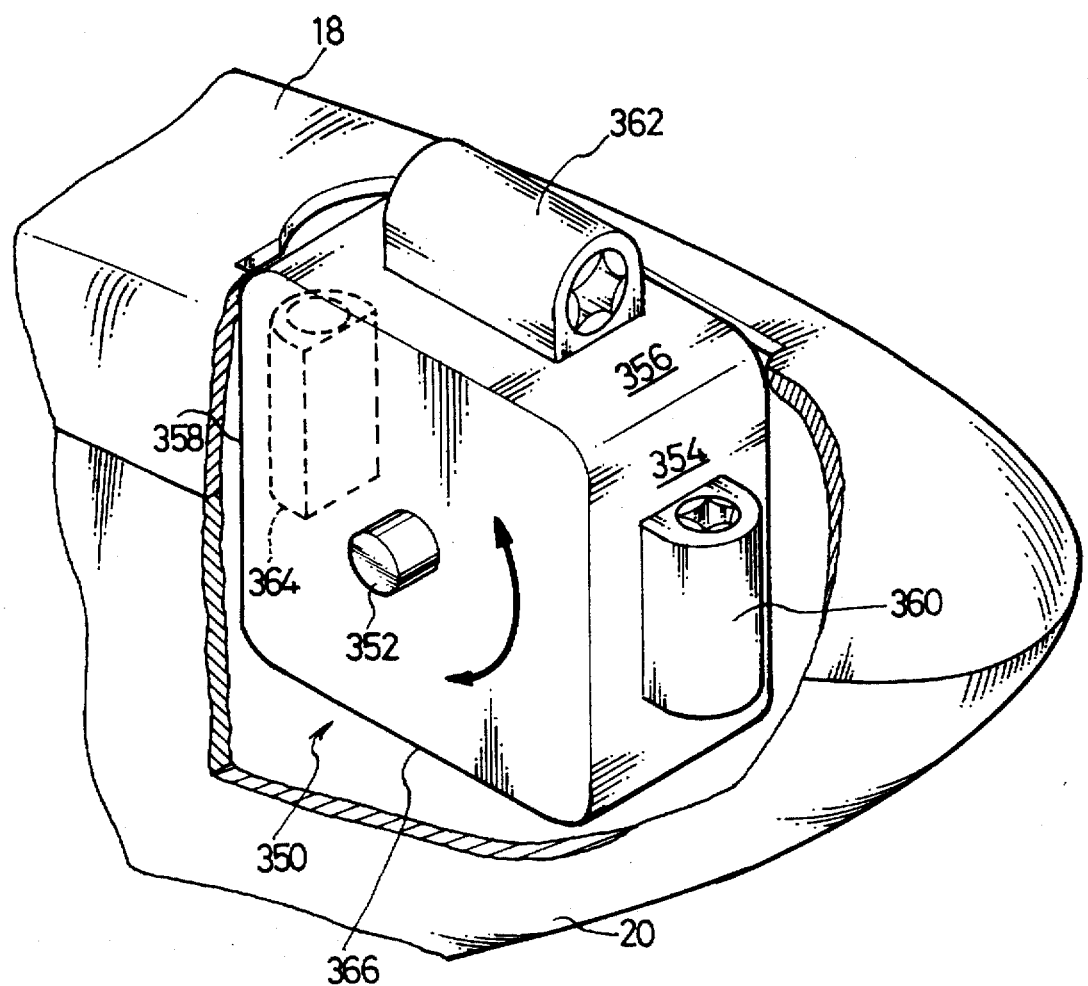
FIG. 19 is a perspective views of the sphygmomanometer according to the fourth embodiment of the invention, with the housing partly cut away to show the revolving member.

FIG. 19 illustrates the digital sphygmomanometer according to the fourth embodiment of the invention. In this embodiment also, the cuffs are mounted to a revolving member journaled rotatably to the housing. To describe only the difference from the third embodiment, the revolving member 350 in this embodiment has a generally quadrangular cross-section and has a rotary shaft 352 extending in the transverse direction. Three cuffs 360, 362 and 364 different in size are mounted, respectively, to the three outer surfaces 354, 356 and 358 of the revolving member in a releasable manner similar to the third embodiment. These three cuffs has the same aspect ratio (L/D≈1.2) but may have an inner diameter of, for example, 16 mm, 22 mm and 28 mm, respectively. In use, the revolving member 350 is rotated in a similar manner to select a cuff of a proper size. When not is use, the revolving member 350 is rotated until the fourth surface 366 thereof is brought into registration with the upper surface of the housing. In this state, all the three cuffs will be retracted within the housing.

Figure 20:
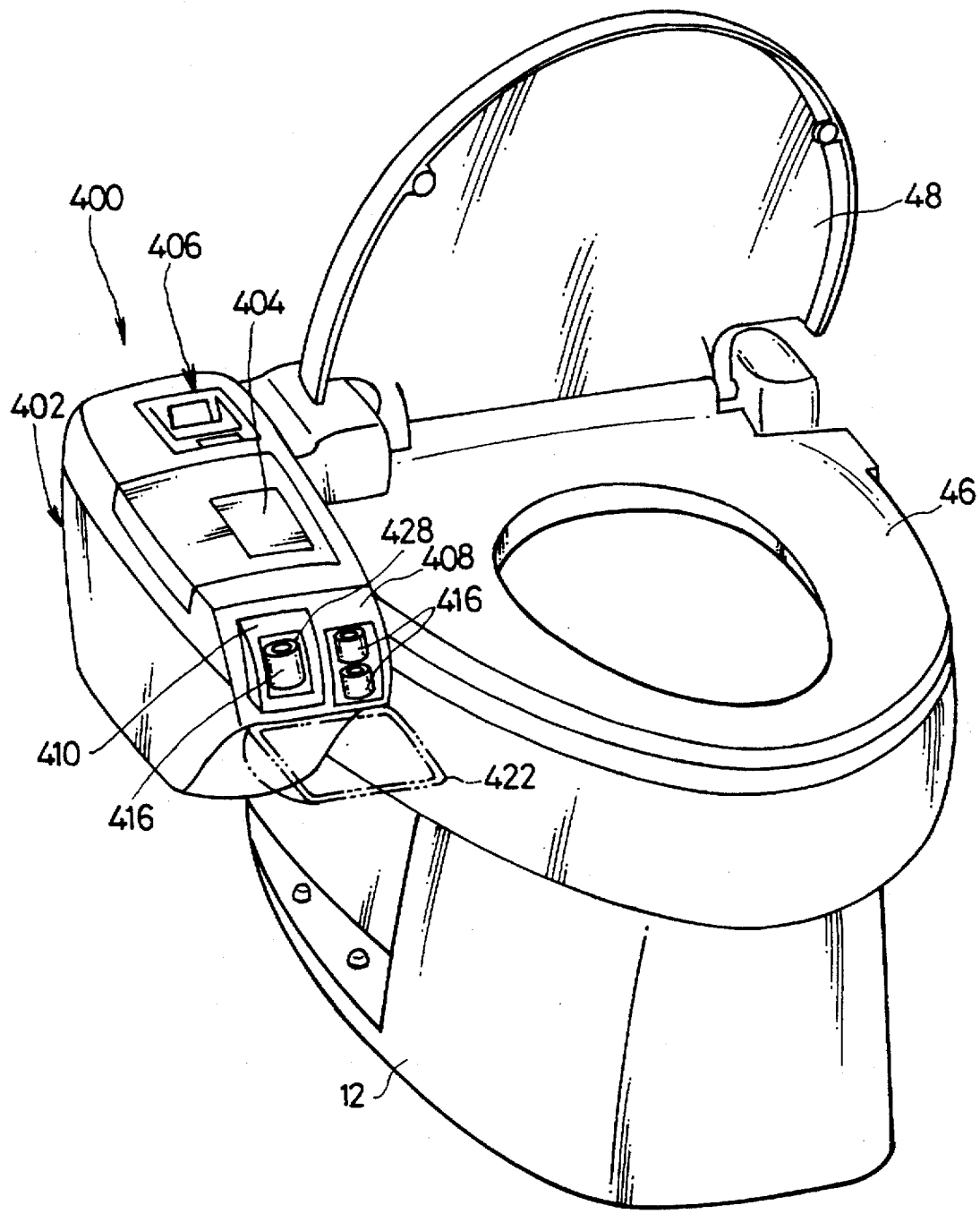
FIG. 20 is a perspective views of the sphygmomanometer according to the fifth embodiment of the invention as installed in a toilet.

FIGS. 20–27 illustrates the digital sphygmomanometer according to the fifth embodiment of the invention. The feature of this embodiment is that one of a plurality of cuffs having different size is replaceably and selectively mounted to a single slider. Referring to FIG. 20, the sphygmomanometer 400 includes a housing 402 fixed to the toilet bowl fixture 12. In the illustrated embodiment, a liquid crystal display device 404 having an input and control device such as a touch input panel as well as a printer 406 for printing the results of measurement are arranged on the top of the housing 402.

Figure 21:
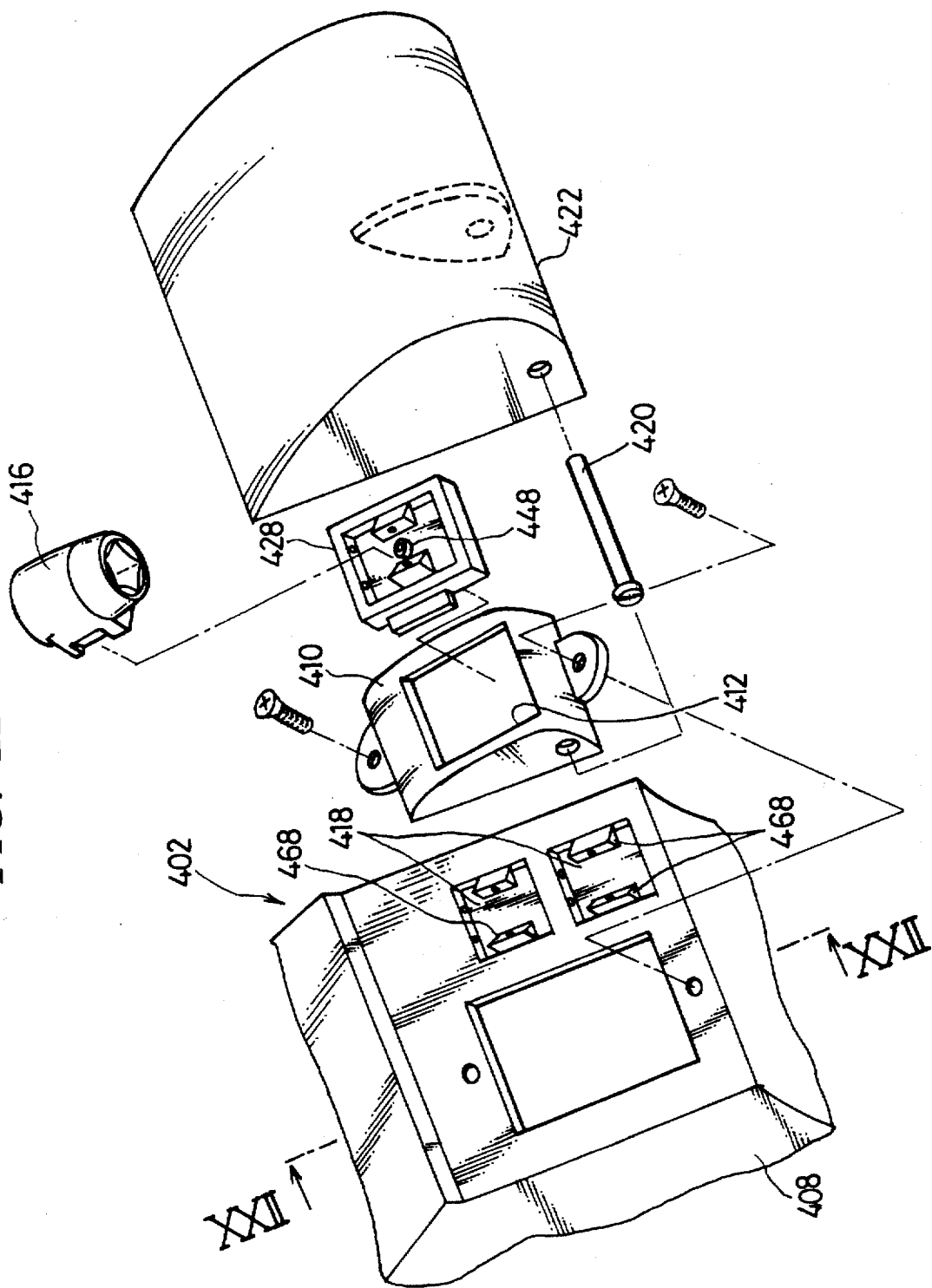
FIG. 21 is an exploded perspective view of the front part of the housing shown in FIG. 20.

The front part of the housing 402 is configured to present a support surface 408 on which a hand-rest 410 is fixed by screws and the like to support the user's palm during blood pressure measurement. The hand-rest 410 is formed with an opening 412 as best shown in FIG. 21 to permit the slider 414 to move therethrough. The sphygmomanometer 400 is provided, for example, with three cuffs 416 different in size, any one of which is selectively mounted to the slider 414 as described later. The remaining two cuffs 416 are affixed to a pair of spare cuff mounting sections 418 provided on the support surface 408 laterally of the hand-rest 410.

As best shown in FIGS. 20 and 21, the support surface 408 is inclined forwardly and downwardly. A swingable cover 422 is hinged by a pivot 420 to the hand-rest 410 to conceal the hand-rest 410 and the spare cuffs 416 arranged on the support surface 408 when the sphygmomanometer is not in use. The pivot 420 rotatably supports the lower end of the cover 422 such that the cover is swung forwardly and downwardly as shown in FIG. 23 when the cover 422 is open.

Figure 22:
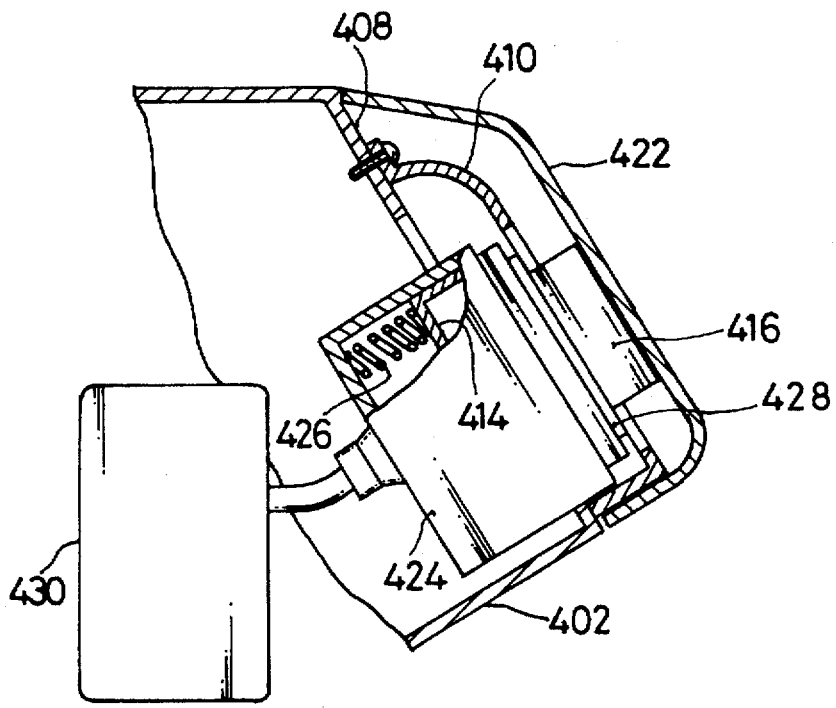
FIGS. 22 and 23 are cross-sectional views taken along the line XXII—XXII of FIG. 21 and showing the cover as closed and opened, respectively.
Figure 23:
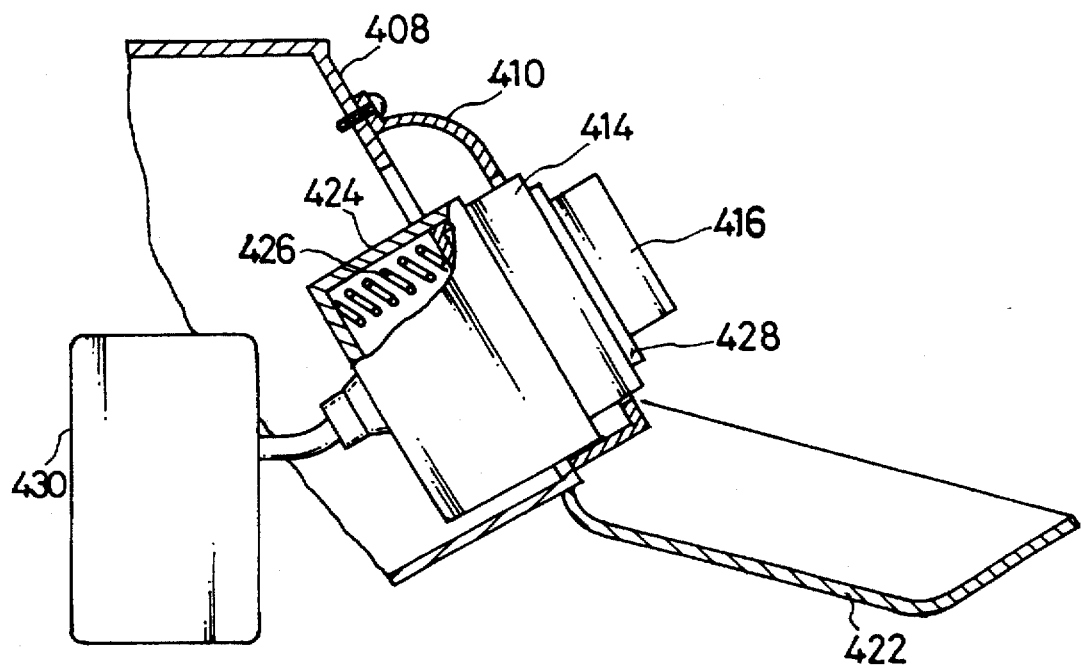

As shown in FIGS. 22 and 23, a slider housing 424 is fixed to the housing 402 and the slider 414 is slidably received in the slider housing 424 and is biased outwardly by a plurality of coiled springs 426. A cuff mounting base 428 is secured to the slider 414 and a cuff 416 selected by the user as having an appropriate size is detachably and releasably mounted to the cuff mounting base 428 as described later with reference to FIGS. 25 and 26. The major components of the digital sphygmomanometer including the air pump and the control and processing circuit may be disposed within a casing 430 arranged within the housing 402.

The cover 422 is made shallow enough to ensure that it abuts against the cuff 416 when the slider 414 has fully stroked. Accordingly, when the cover 422 is closed as shown in FIG. 22, the cover 422 will be brought into contact with the cuff 416 to push it down together with the mounting base 428 and the slider 414 thereby to retract the cuff 416 partly within the housing. In this condition, all of the cuffs 416 are concealed by the cover 422 thereby avoiding the risk that the cuffs are fouled. Furthermore, the cuffs 416 and the cover 422 do not hinder ordinary use of the toilet as they are provided on the inclined support surface 408 arranged at the front part of the housing 402.

Figure 27:
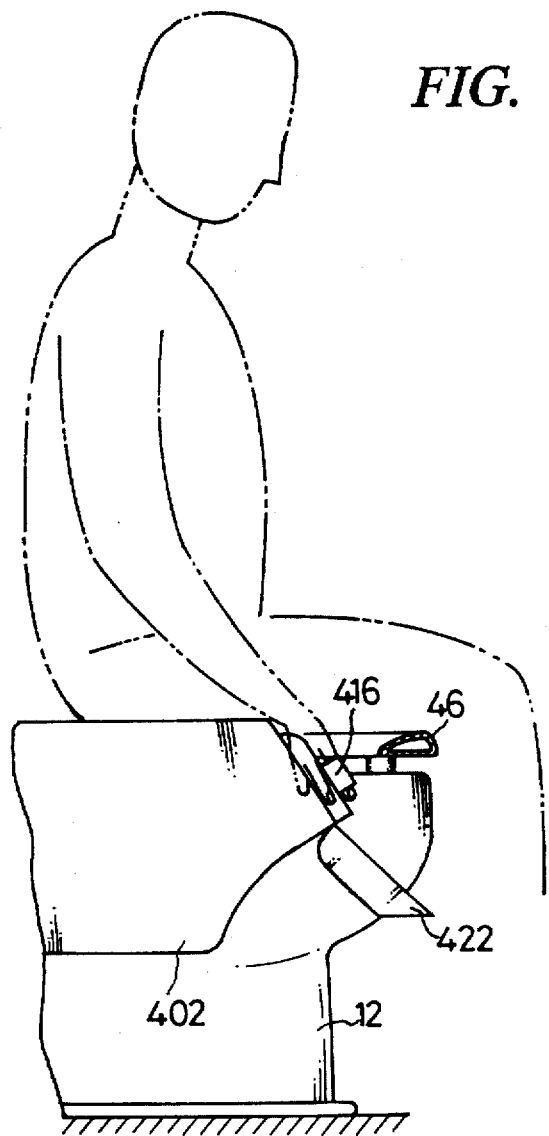
FIG. 27 is a schematic side elevational view showing the use of the sphyomanometer.

When the cover 422 is open as shown in FIG. 23, the slider 414 will be pushed out under the action of the coiled spring 426 causing the cuff 416 to be emerged out of the opening 412 of the hand-rest 410. In this state, the user seated on the toilet seat 46 may engage the second finger into the cuff 416 as shown in FIG. 27 to permit measurement of the artery blood pressure. Since the support surface 408 of the housing 402 is forwardly inclined, it will be easy for the user to engage its finger into the cuff 416 while the arm of the user as seated on the toilet seat is suspended in a relaxed fashion as will be readily understood from FIG. 27, so that the blood pressure measurement may be carried out with an easy posture.

Figure 24:
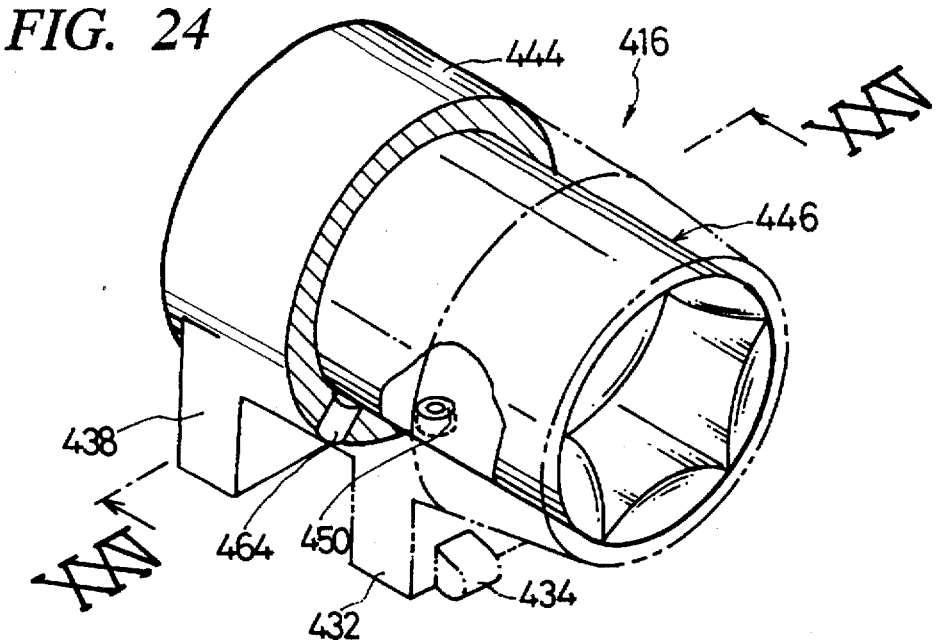
Figure 26:
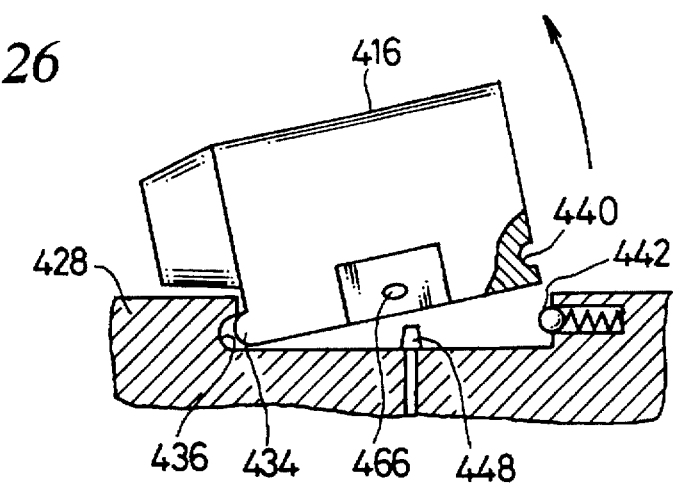
FIG. 26 is a cross-sectional view taken along the line XXVI—XXVI of FIG. 25.

The cuff 416 is mounted to the cuff mounting base 428 in a releasable and replaceable manner by balled lock mechanisms. To this end, as shown in FIGS. 24 and 26, a pair of rounded projections 434 are provided on the front leg 432 of the cuff and a pair of associated notches 436 are formed on the cuff mounting base 428 for engagement with the projections 434. Also, as shown in FIG. 26, the rear leg 438 of the cuff is provided with a pair of notches 440 which are adapted to be engaged by a pair of 35 spring biased balls 442.

With this arrangement, upon depressing the rear part of the cuff 416 after bringing the projections 434 into engagement with the notches 436, the balls 442 will be snap fitted into the notches 440 whereby the cuff 416 is mounted to the mounting base 428 in a very simple manner. To exchange the cuff, the cuff 416 may be dismounted from the base 428 simply by pulling up the rear part thereof. Furthermore, the cuff 416 will be readily released from the base 428 whenever an excessive force is applied to the cuff such as the case where the user abruptly stands up with the finger engaged into the cuff 416.

Figure 25:
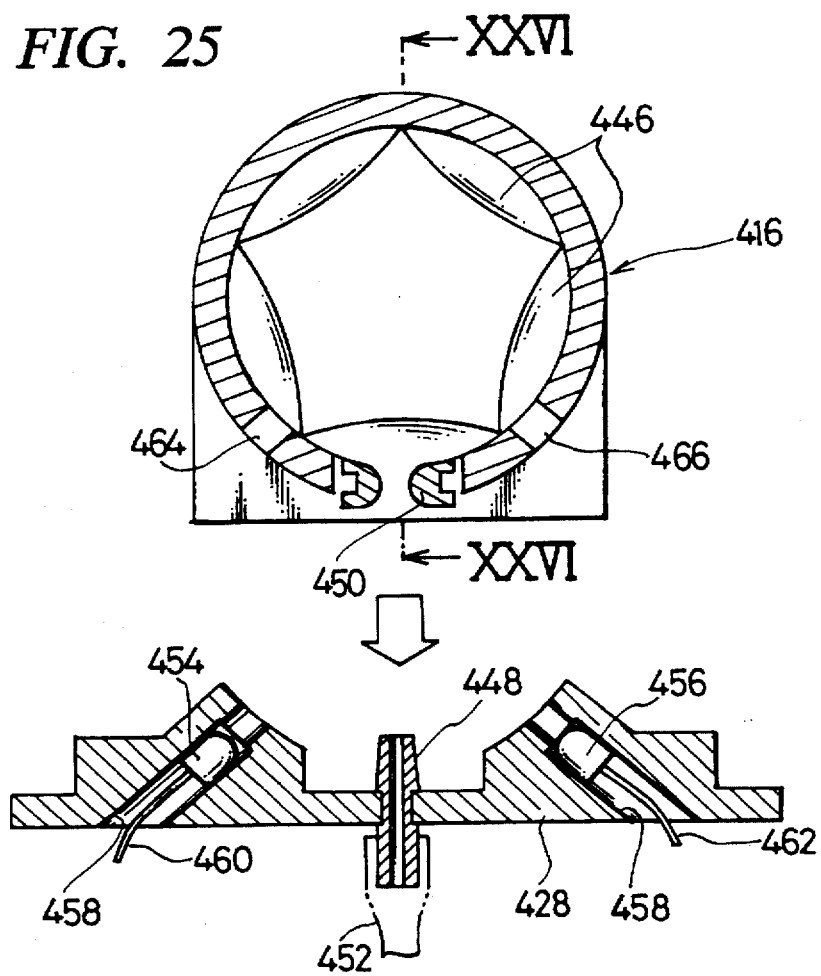
FIG. 25 is a cross-sectional view taken along the line XXV—XXV of FIG. 24 and showing the manner in which the cuff is mounted to a cuff mounting base.

Referring to FIGS. 24 and 25, in the illustrated embodiment, each of the cuffs 416 includes a tubular case 444 made of rigid material such as hard plastics and a bladder 446 arranged inside of the case. The bladder may be made by high frequency welding of a light transmitting sheet of polyurethane in a manner described before with reference to FIG. 5.

As best shown in FIG. 25, the cuff mounting base 428 is provided with a nipple 448 which is designed to engage with an air joint 450 of the bladder 446 as the cuff 416 is mounted on the mounting base 428. When the bladder 446 is to be distended, air under pressure is supplied to the nipple 448 through a hose 452 connected to the air pump, not shown, arranged in the casing 430.

In the illustrated embodiment, a near-infrared light emitting diode (iRED) 454 and a phototransistor 456 are arranged on the cuff mounting base 428 as shown in FIG. 25. To this end, the cuff mounting base 428 is formed with a pair of sensor mounting holes 458 in which the iRED 454 and the phototransistor 456 are fitted, respectively. Lead wires 460 and 462 of these elements are extended across the mounting base 428 and the slider 414 and are connected, respectively, to the control and processing circuit in the casing 430. Accordingly, the iRED 454 and the phototransistor 456 as well as the lead wires thereof need not be arranged in respective cuffs 416. As a result, the structure of the cuffs 416 is simplified and the exchangeable cuffs may be made at a low cost.

As shown in FIGS. 24 and 25, the case 444 of each cuff 416 is formed with a light emitting window 464 and a light receptive window 466 corresponding, respectively, to the mounting holes 458 to ensure that, when the cuff 416 is mounted to the base 428, the near-infrared light from the iRED 454 is emitted upon the finger and the reflected or transmitted light is directed to the phototransistor 456. As the bladder 446 of the cuffs 416 is made of an opaque polyurethane sheet, emission and reception of light are permitted only by providing respective cuffs 416 with the windows 464 and 466.

Referring again to FIG. 21, each of the spare cuff mounting sections 418 has a pair of positioning projections 468 designed to detachably affix by snap fit the spare cuff 416 on the spare cuff mounting section. The user may select a cuff of a proper size suited to the diameter of the user's finger and mount the selected cuff to the cuff mounting base 428 for use.

While the present invention has been described herein with reference to the specific embodiments thereof, it is contemplated that the present invention is not limited thereby and various changes and modification may be made therein. For instance, the number and structure of the cuffs, sliders and pivoting arms may be varied as required. The configuration of the revolving member may be modified. While the measurement of the artery blood pressure and pulse rate has been described as being carried out by the volume oscillometric method, it is equally possible to use the pressure oscillometric method.

I claim:

1. In a toilet-installed digital sphygmomanometer having an occluding cuff mounted to a housing adapted to be installed laterally of a toilet seat and processing means associated with said cuff for measuring blood pressure, the improvement comprising:

movable support means arranged in said housing for supporting said cuff to allow for movement of the cuff between an operative position in which said cuff is emerged out of said housing for engagement by the user with its finger and a rest position in which said cuff is retracted substantially within said housing, wherein said cuff is supported by said moveable support means in both the operative and rest positions.

2. A sphygmomanometer according to claim 1, wherein said movable support means comprises a slider mounted to said housing for sliding movement with respect thereto to displace said cuff between said operative and rest positions.

3. A sphygmomanometer according to claim 2, further comprising a second occluding cuff which is different in size from said first-mentioned cuff and a second slider carrying said second cuff for movement between the operative and rest positions thereof.

4. A sphygmomanometer according to claim 3, wherein said first and second sliders are juxtaposed laterally with one another so that said cuffs are arranged in a side-by-side relationship.

5. A sphygmomanometer according to claim 4, wherein said sphygmomanometer includes a single air pump feeding said first and second cuffs, said first and second cuffs being connected, respectively, to said air pump through first and second shut-off valves, said valves being interconnected, respectively, with said first and second sliders in such a manner that the associated cuff is in communication with said air pump only when said associated cuff is brought in said operative position.

6. A sphygmomanometer according to claim 4, wherein said first and second sliders are interlocked with each other in such a manner to prevent both of said cuffs from simultaneously being in the operative position.

7. A sphygmomanometer according to claim 2, wherein said housing includes a forwardly and downwardly inclined front surface and wherein said cuff is arranged on said inclined front surface for ease of the user's posture during artery blood pressure measurement.

8. A sphygmomanometer according to claim 7, wherein said cuff is covered by a swingable cover hinged at its lower end to said housing.

9. A sphygmomanometer according to claim 8, wherein said cover is operative to engage said cuff to retract it within said housing as said cover is rotated into a closed position thereof.

10. A sphygmomanometer according to claim 7, wherein said sphygmomanometer comprises a plurality of cuffs different in size, one of said cuffs being detachably mounted to said slider, with the other being detachably affixed to said inclined front surface to permit the user to select a cuff of a proper size.

11. A sphygmomanometer according to claim 1, wherein said movable support means comprises a revolving member journaled for rotational movement to said housing, said cuff being mounted to said revolving member such that upon rotation of said revolving member said cuff is emerged out of said housing and upon further rotation said cuff is retracted within said housing.

12. A sphygmomanometer according to claim 11, wherein said revolving member has a first surface on which said cuff is mounted and a second surface which is brought in flush with an outer surface of said housing when said member is rotated at said another angle.

13. A sphygmomanometer according to claim 11, wherein said revolving member has a generally triangular cross-section defined by first, second and third surfaces and wherein said sphygmomanometer comprises first and second cuffs different in size, said first and second cuffs being mounted, respectively, to said first and second surfaces.

14. A sphygmomanometer according to claim 11, wherein said revolving member has a generally quadrangular cross-section defined by first, second, third and fourth surfaces and wherein said sphygmomanometer comprises first, second and third cuffs different in size, said cuffs being mounted, respectively, to said first, second and third surfaces.

15. A sphygmomanometer according to claim 11, wherein said revolving member has a polygonal cross-section and wherein said sphygmomanometer comprises a plurality of cuffs different in size mounted to outer surfaces of said revolving member.

16. A sphygmomanometer according to claim 1, wherein said movable support means comprises a pivoting arm having a frontal end pivoted to said housing and a rear end supporting said cuff.

17. A sphygmomanometer according to claim 1, wherein said movable support means comprises a plurality of pivoting arms each having a frontal end pivoted to said housing and wherein said sphygmomanometer comprises a plurality of cuffs different in size and mounted, respectively, to the rear ends of said pivoting arms.

18. A sphygmomanometer according to one of claims 1 or 2, wherein said cuff is releasably attached by snap-fit to said movable support means in such a manner that upon application of force, said cuff is dismounted from said support.

* * * * *